United States Patent [19]

Kanno

[11] Patent Number: 5,374,965
[45] Date of Patent: Dec. 20, 1994

[54] MEDICAL NETWORK SYSTEM WITH COMMON ANALOG INFORMATION TRASMISSION LINE

[75] Inventor: Masahide Kanno, Hachioji, Japan

[73] Assignee: Olympus Optical Co., Ltd., Tokyo, Japan

[21] Appl. No.: 799,454

[22] Filed: Nov. 25, 1991

[30] Foreign Application Priority Data

Nov. 26, 1990 [JP] Japan .................. 2-324626

[51] Int. Cl.$^5$ .............................. H04N 7/18
[52] U.S. Cl. ..................... 348/705; 379/100; 358/435; 348/71
[58] Field of Search ............... 358/400, 401, 75, 450, 358/409, 407, 434, 435, 436, 141, 12, 98, 500, 181; 382/55; 379/100; 364/413.13; 348/65, 71, 74, 552, 705; H04N 7/18

[56] References Cited

U.S. PATENT DOCUMENTS

| | | | |
|---|---|---|---|
| 4,051,522 | 9/1977 | Healy et al. | 358/86 |
| 4,302,781 | 11/1981 | Ikeda et al. | 358/409 |
| 4,488,179 | 12/1984 | Kruger et al. | 358/181 |
| 4,764,870 | 8/1988 | Haskin | 364/413.13 |
| 4,802,008 | 1/1989 | Walling | 358/134 |
| 4,900,902 | 2/1990 | Sakakibura | 379/100 |
| 4,945,410 | 7/1990 | Walling | 358/134 |
| 5,005,126 | 4/1991 | Haskin | 364/413.13 |
| 5,007,407 | 4/1991 | Kikuchi | 358/98 |
| 5,041,914 | 8/1991 | Ban | 358/75 |
| 5,061,994 | 10/1991 | Takahashi | 358/98 |
| 5,081,524 | 1/1992 | Tsuruoka et al. | 358/98 |
| 5,138,654 | 8/1992 | Yuki | 379/100 |

FOREIGN PATENT DOCUMENTS 61-187434 8/1986 Japan .

*Primary Examiner*—Victor R. Kostak
*Assistant Examiner*—Jeffrey S. Murrell
*Attorney, Agent, or Firm*—Armstrong, Westerman, Hattori, McLeland & Naughton

[57] ABSTRACT

A medical network system has an image sending device for sending medical image information, such as endoscopic image information, an image receiving device for receiving the medical image information, a centralized control device having sending and receiving functions for centrally controlling the transmission of the medical image information among the above devices, and an analog transmission line for transmitting the medical image information among the devices at high speed. The centralized control device controls the transmission of the medical image information by using digital signals.

10 Claims, 28 Drawing Sheets

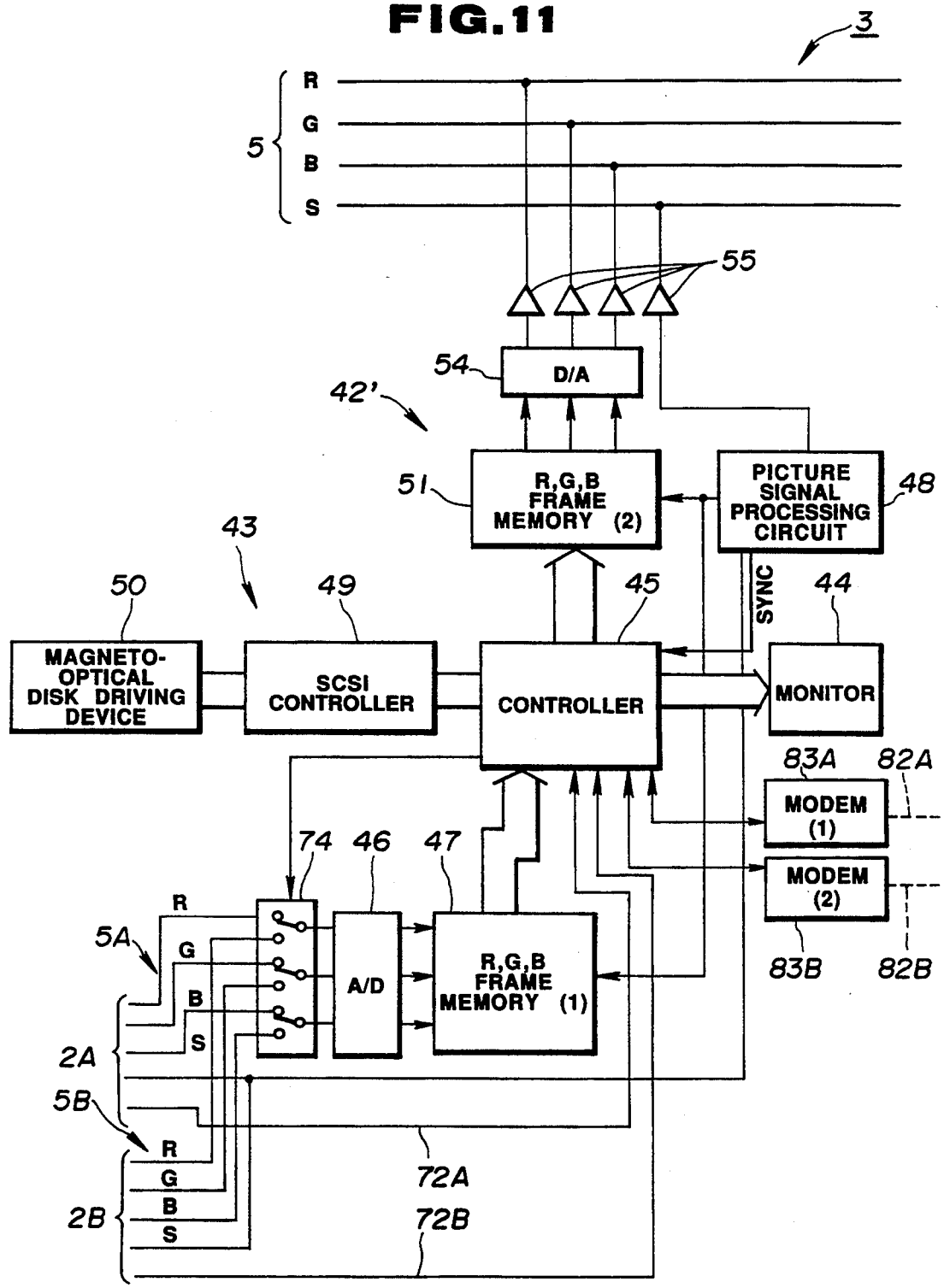

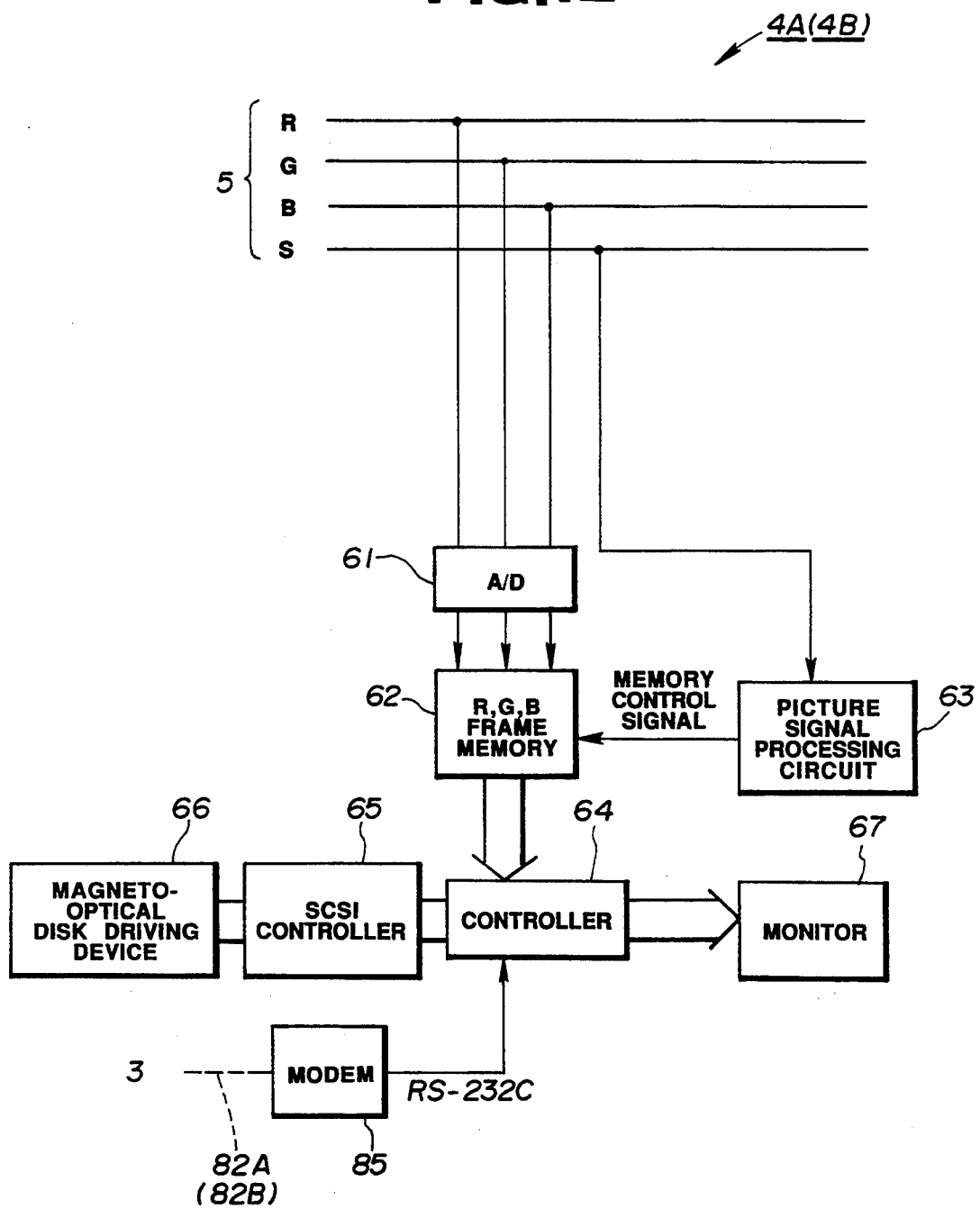

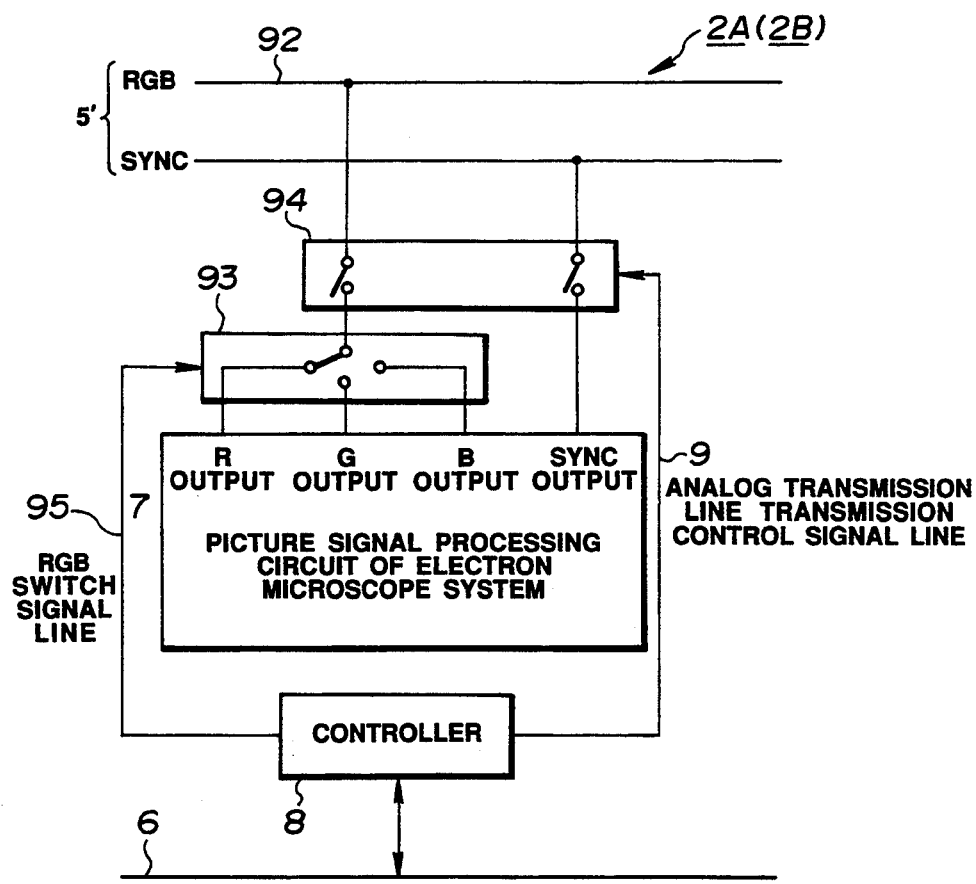

DIGITAL DATA

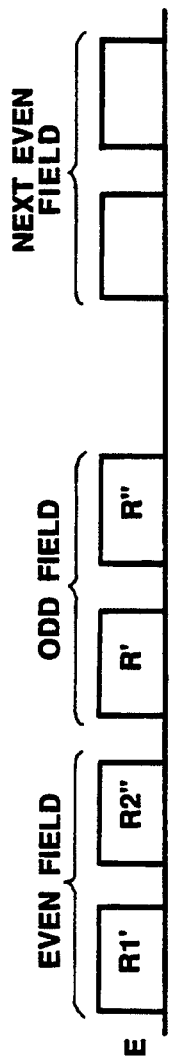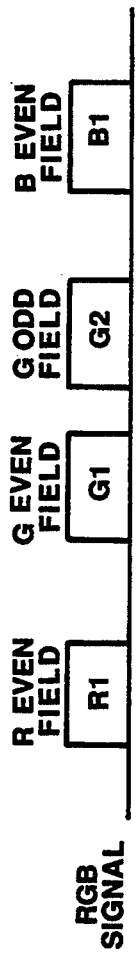

MEDICAL NETWORK SYSTEM WITH COMMON ANALOG INFORMATION TRASMISSION LINE

BACKGROUND OF THE INVENTION

1. Field of the Invention

The present invention relates to a medical network system which transmits image information by using an analog transmission line and so on.

2. Description of the Related Art

An endoscopic examination for directly observing the inside of a living body has recently become more important in diagnosis. In particular, the appearance of an electron endoscope enables many people to make observation on a television monitor, and image processing and the like with the electron endoscope have been studied. In such a situation, the endoscopic examination is carried out not only in an endoscopic examination room, but also in an X-ray examination room, an operating room and so on, and furthermore, images obtained by the endoscope are read in a wide range of places, for example, in an endoscopic examination room, a conference room and a lecture hall. Therefore, efficient endoscopic examinations in various places and easy endoscopic image observation have been strongly demanded.

Turning attention to the outside situation surrounding the endoscopic field, large-scale office automation using various kinds of medical information systems, such as PACS (Picture Archiving & Communication System) and PHD (Personal Health Data management system), have been planned in hospitals.

However, PACS, whose use is mainly examined in the X-ray field, requires a huge investment in equipment, a great amount of time to transfer image data and so on, and thus has not yet been practically used.

In the case of PACS, since patient data (for example, ID No. and name) and a vast amount of image information are transmitted digitally, it takes several minutes to transmit one image.

Furthermore, PHD also has not reached practical use due to problems in recording media and system operation.

Japanese Laid-open Patent No. Sho 61-187434 discloses a system which transmits image information in both analog and digital signals, distinguishes the kind of the signal by using components of a system, and performs image processing according to the resulting distinction.

In the above prior art, although image information can be analogously transmitted in a short time, it takes much time to digitally transmit the image information.

OBJECT AND SUMMARY OF THE INVENTION

It is an object of the present invention to provide a medical network system capable of being materialized at low cost and of transferring image information at high speed.

It is another object of the present invention to provide an endoscopic image transmission network system capable of being materialized at low cost and of transmitting image information at high speed.

In order to achieve the above objects, there is provided a network system which is comprised of at least one image sending means and one image receiving means, a plurality of either or both of the image sending means or the image receiving means, an image transmission means for transmitting medical image information through an analog transmission line, and an image transmission control means for controlling the transmission of the image information by digital signals. Therefore, it is possible to transmit image information in a short time, and to simplify the construction of a control system for image information, thereby reducing costs.

BRIEF DESCRIPTION OF THE DRAWINGS

FIG. 1 is a schematic view of an endoscopic image network system according to the first embodiment;

FIG. 2 is a schematic view of the principal part of an electron microscope system according to the first embodiment;

FIG. 3 is a specific view of the electron microscope system;

FIG. 4 is a schematic view of a centralized control system of the first embodiment; and FIG. 5 is a schematic view of a conference system of the first embodiment.

FIG. 6 is a schematic view of an endoscopic image network system according to the second embodiment;

FIG. 7 is a schematic view of the principal part of an electron microscope system according to the second embodiment;

FIG. 8 is a schematic view of a centralized control system of the second embodiment; and FIG. 9 is a schematic view of a conference system of the second embodiment.

FIGS. 10 to 12 each show a third embodiment of the present invention.

FIG. 10 is a schematic view of an endoscopic image network system according to the third embodiment;

FIG. 11 is a schematic view of a centralized control system of the third embodiment; and FIG. 12 is a schematic view of a conference system of the third embodiment.

FIGS. 13 to 17 each show a fourth embodiment of the present invention.

FIG. 13 is a schematic view of an endoscopic image network system according to the fourth embodiment;

FIG. 14 is an explanatory view of signal transmission of the fourth embodiment;

FIG. 15 is a schematic view of the principal part of an electron microscope system according to the fourth embodiment;

FIG. 16 is a schematic view of a centralized control system of the fourth embodiment; and FIG. 17 is a schematic view of a conference system of the fourth embodiment.

FIG. 18 is an explanatory view of the signal form according to the fifth embodiment;

FIG. 19 is a schematic view of the principal part of an electron microscope system according to the fifth embodiment;

FIG. 20 is a schematic view of a centralized control system of the fifth embodiment; and FIG. 21 is a schematic view of a conference system of the fifth embodiment.

FIG. 22 is an explanatory view of the signal form according to the sixth embodiment;

FIG. 23 is a schematic view of the principal part of an electron microscope system according to the sixth embodiment;

FIG. 24 is a schematic view of a centralized control system of the sixth embodiment; and FIG. 25 is a schematic view of a conference system of the sixth embodiment.

FIGS. 26 to 28 each show a seventh embodiment of the present invention.

FIG. 26 is an explanatory view of the process contents of signal transmission according to the seventh embodiment;

FIG. 27 is an explanatory view graphically showing FIG. 26; and

FIG. 28 is an explanatory view of the signal transmission shown in FIG. 26.

FIG. 29 is an explanatory view of signal transmission according to an eighth embodiment of the present invention.

FIG. 30 is a schematic view of the principal part of a conference system of the ninth embodiment; and FIG. 31 is an explanatory view showing the operations of the ninth embodiment.

FIG. 32 is a schematic view of an endoscopic image network system according to the tenth embodiment;

FIG. 33 is a schematic view of the principal part of the endoscopic image network system shown in FIG. 32; and FIG. 34 is an explanatory view showing the operations of the tenth embodiment.

FIG. 35 is a schematic view of an endoscopic image network system according to the eleventh embodiment;

FIG. 36 is a schematic view of a centralized control system of the eleventh embodiment;

FIG. 37 is a schematic view of a conference system of the eleventh embodiment; and FIG. 38 is an explanatory view of a typical operation of the eleventh embodiment.

DESCRIPTION OF THE PREFERRED EMBODIMENTS

Preferred embodiments of the present invention will now be specifically described with reference to the accompanying drawings.

Figure 1:
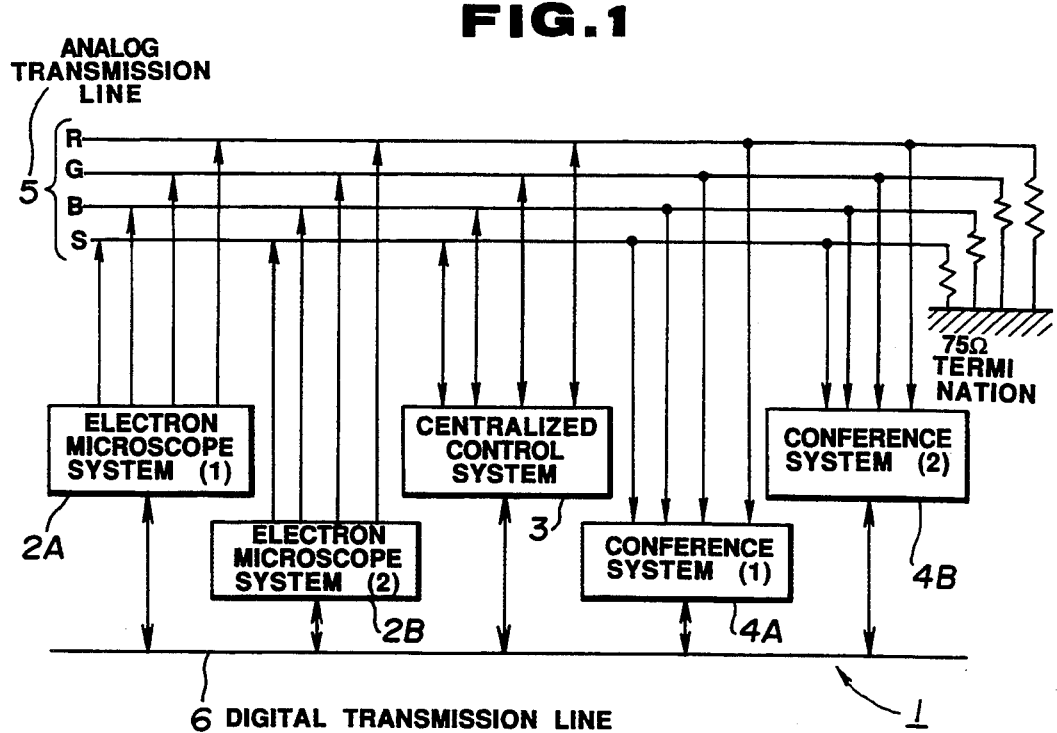
FIGS. 1 to 5 each show a first embodiment of the present invention.

As shown in FIG. 1, an endoscopic image network system 1 serving as a medical network system according to a first embodiment of the present invention is comprised of a plurality of electron microscope systems (1) 2A and (2) 2B each having an image pickup means for generating an endoscopic image, a centralized control system 3 for centrally controlling the whole system 1, a plurality of conference systems (1) 4A and (2) 4B for image observation, an analog transmission line 5 for transmitting image information among the above systems, and a digital transmission line 6 for transmitting digital signals used to control the transmission of the image information.

The analog transmission line 5 is composed of four coaxial lines of, for example, 75 Ω which respectively transmit R, G and B picture signals corresponding to color image information and a synchronizing signal SYNC (abbreviated as "S" or "SYNC") in synchronization with the picture signals (the lines for transmitting the signals R, G, B and S will be abbreviated as "R, G, B and S lines", respectively), and each terminated by a resistor of 75 Ω.

The digital transmission line is a two-way transmission line generally controlled by a controller of the centralized control system 3 as a server. The digital transmission line 6 is used to control the dedication right (transmission right, receiving right) of the analog transmission line 5 and to transmit data related to the above image information, such as patient data.

The construction of each of the above systems will be explained.

Figure 2:
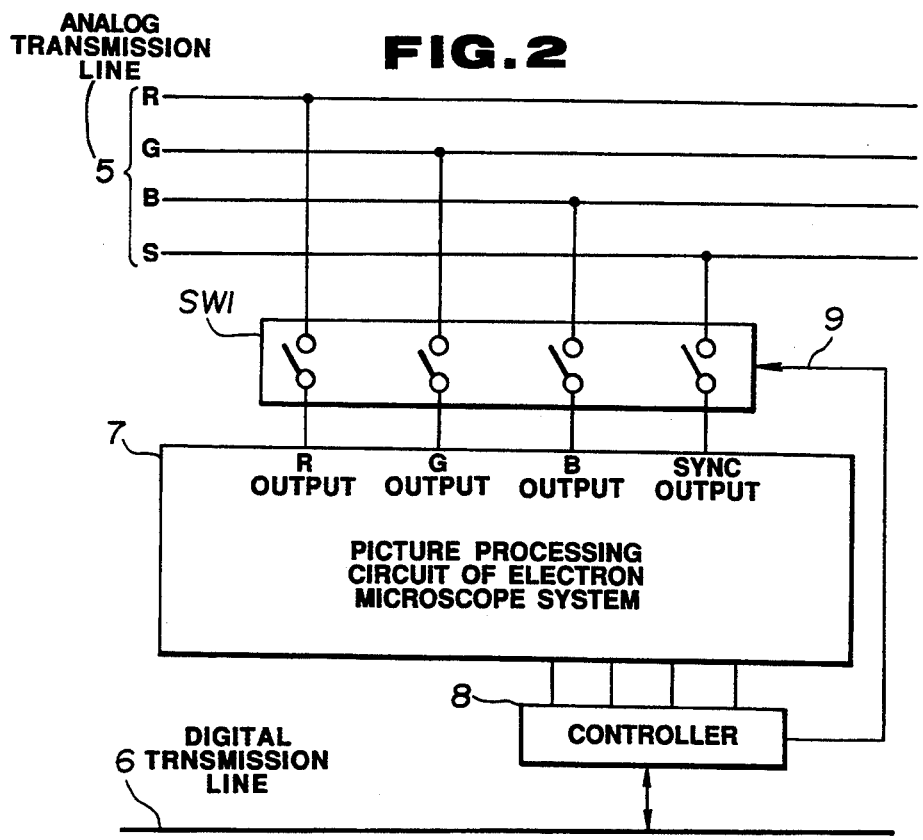

FIG. 2 shows the construction of the principal part of the electron microscope system (1) 2A or (2) 2B.

R, G, B and SYNC output terminals of a picture processing circuit 7 of the electron microscope system (1) 2A or (2) 2B are connected to the R, G, B and S lines of the analog transmission line 5, respectively, through an analog switch SW1 having four circuits. The opening and closing of the analog switch SW1 are controlled by a controller 8 through an analog transmission line transmission control signal line 9.

The controller 8 connected to the digital transmission line 6 transmits control signals to the centralized control system 3. For example, the controller 8 can send a command to obtain a transmission right for registering a static image to the centralized control system 3 through the digital transmission line 6, receive a reply command indicating that the transmission is available from the centralized control system 3, turn on the analog switch SW1, and send the static image to the centralized control system 3 through the analog transmission line 5, thereby registering the static image in the centralized control system 3.

Figure 3:
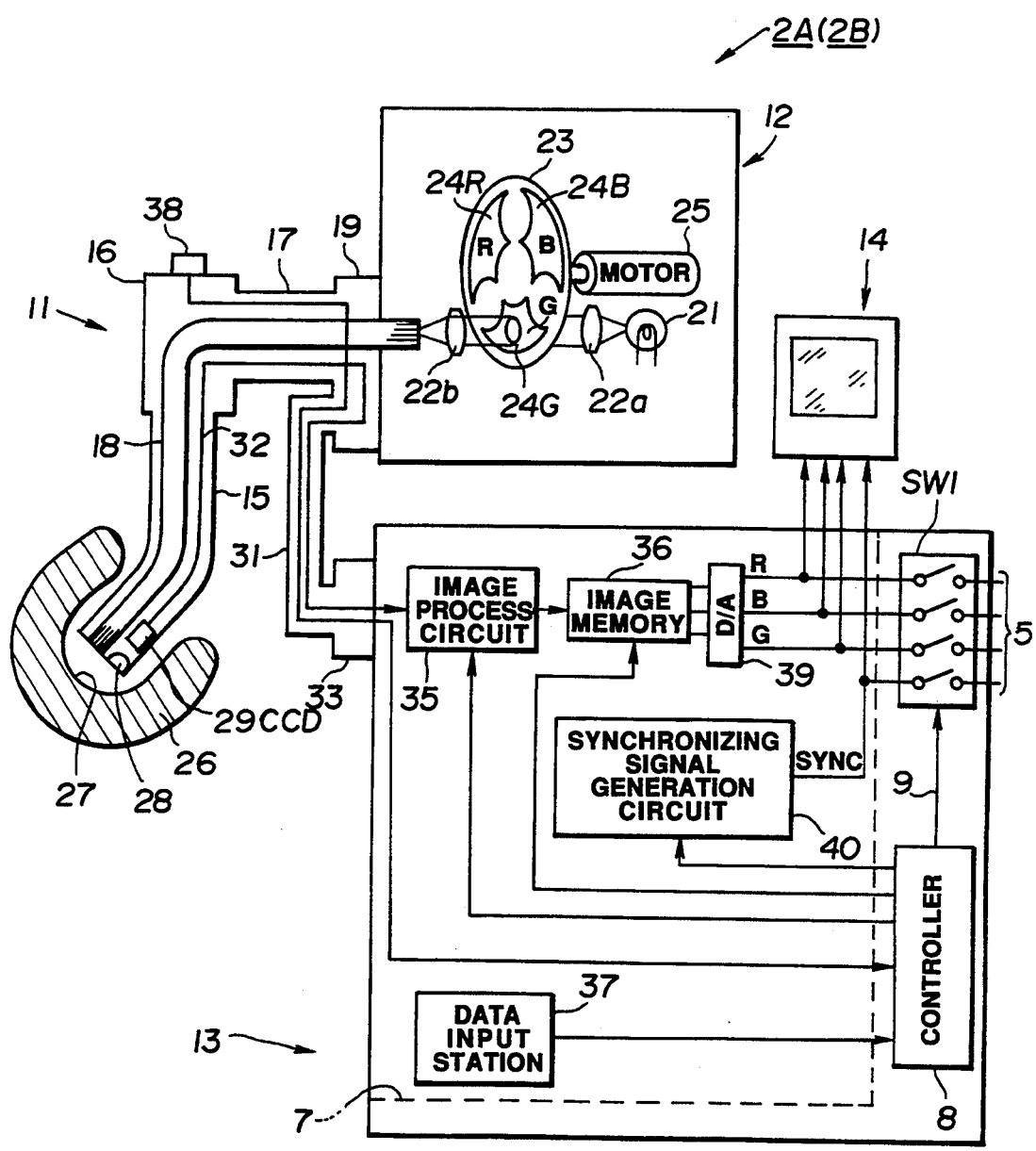

FIG. 3 shows the detailed construction of the electron microscope system (1) 2A or (2) 2B.

The electron microscope system 2A or 2B is comprised of an electron microscope 11 having an image pickup means therein, a light source device 12 for supplying illumination light to the electron microscope 11, a picture signal processing circuit 13 for performing signal processing with respect to the electron microscope 11, and a monitor 14 for displaying a picked endoscopic image based on R, G and B picture signals and the synchronizing signal SYNC generated by the picture signal processing circuit 13.

The electron microscope 11 is formed with an elongated inserting portion 15, a wide operating portion 16 formed at the rear end of the inserting portion 15, and a universal code 17 extending from the operating portion 16. A light guide 18 passes through the inserting portion 15 and the universal code 17, and frame sequential illumination light beams are supplied from the light source device 12 by attaching a light source connector 19 connected to the universal code 17 to the light source device 12.

A light source lamp 21 is disposed in the light source device 12, and a collimator lens 22a for collimating the illumination light beams from the light source lamp 21, a rotary filter 23, and a condenser lens 22b for condensing and radiating the illumination light onto the incidence plane of the light guide 18 are arranged in this order from the side of the light source lamp 21 on the optical axis linking the light source lamp 21 and the incidence plane of the light guide 18. The rotary filter 23 is in the shape of a disk formed with color transmitting filters 24R, 24G and 24B respectively for transmitting color light beams of red (R), green (G) and blue (B) which are circumferentially arranged. The illumination light beams collimated by the collimator lens 22a enter the color transmitting filters 24R, 24G and 24B. The rotary filter 23 is rotated by a motor 25, thereby supplying the color light beams of red, green and blue to the light guide 18 in time sequence.

The illumination light beams sent through the light guide 18 are emitted forward from the leading end of the inserting portion 15 so as to illuminate, for example, a part 27 of a living body 26 to be observed. An image of the illuminated part 27 is formed by an objective lens 28 at the leading end of the inserting portion 15 on a CCD 29 as a solid image pickup element disposed on the focal plane of the objective lens 28, and photoelectrically converted.

The CCD 29 is connected to a signal line 32 which passes through the universal code 17 and a signal cable 31 extending from the connector 19, and a signal connector 33 attached to the end of the signal cable 31 is connectable to the picture signal processing circuit 13.

Signals obtained by photoelectric conversion of the CCD 29 are read in response to a drive signal from an unillustrated drive circuit in an image process circuit 35, and provided with processing, such as amplification and white balancing, by an amplifier in the image process circuit 35, and converted from analog to digital, thereby outputting time-sequential R, G and B signals to an image memory 36.

In the image memory 36, patient data, an error message and so on from a data input station 37 composed of a keyboard can be superimposed on the R, G and B signals through the controller 8.

The color signals obtained when the frame sequential light beams are radiated are sequentially written in the image memory 36, and simultaneously read, thereby outputting synchronized digital R, G and B signals.

When a freeze switch 38 mounted on the operating portion 16 of the electron microscope 1 is actuated, the controller 8 outputs a write inhibition signal to the image memory 36, and holds a signal previous to the write inhibition signal as a static image.

The R, G and B signals read from the image memory 36 are converted into analog R, G and B signals by a D/A converter 39, and output to the monitor 14 together with a synchronizing signal SYNC from a synchronizing signal generation circuit 40, thereby displaying the picked endoscopic image.

The analog R, G and B signals converted by the D/A converter 39 and the synchronizing signal SYNC can be sent to the analog transmission line 5 through the analog switch SW1.

Furthermore, the controller 8 is connected to the digital transmission line 6 as shown in FIG. 2, and thus can perform two-way communication with the centralized control system 3.

For example, a command to register a static image and so on can be sent to the centralized control system 3 by using the data input station 37, and the analog switch SW1 can be turned on in response to a reply from the centralized control system 3.

The picture signal processing circuit 7 shown in FIG. 2 corresponds to a part indicated by the dotted line shown in FIG. 3.

Figure 4:
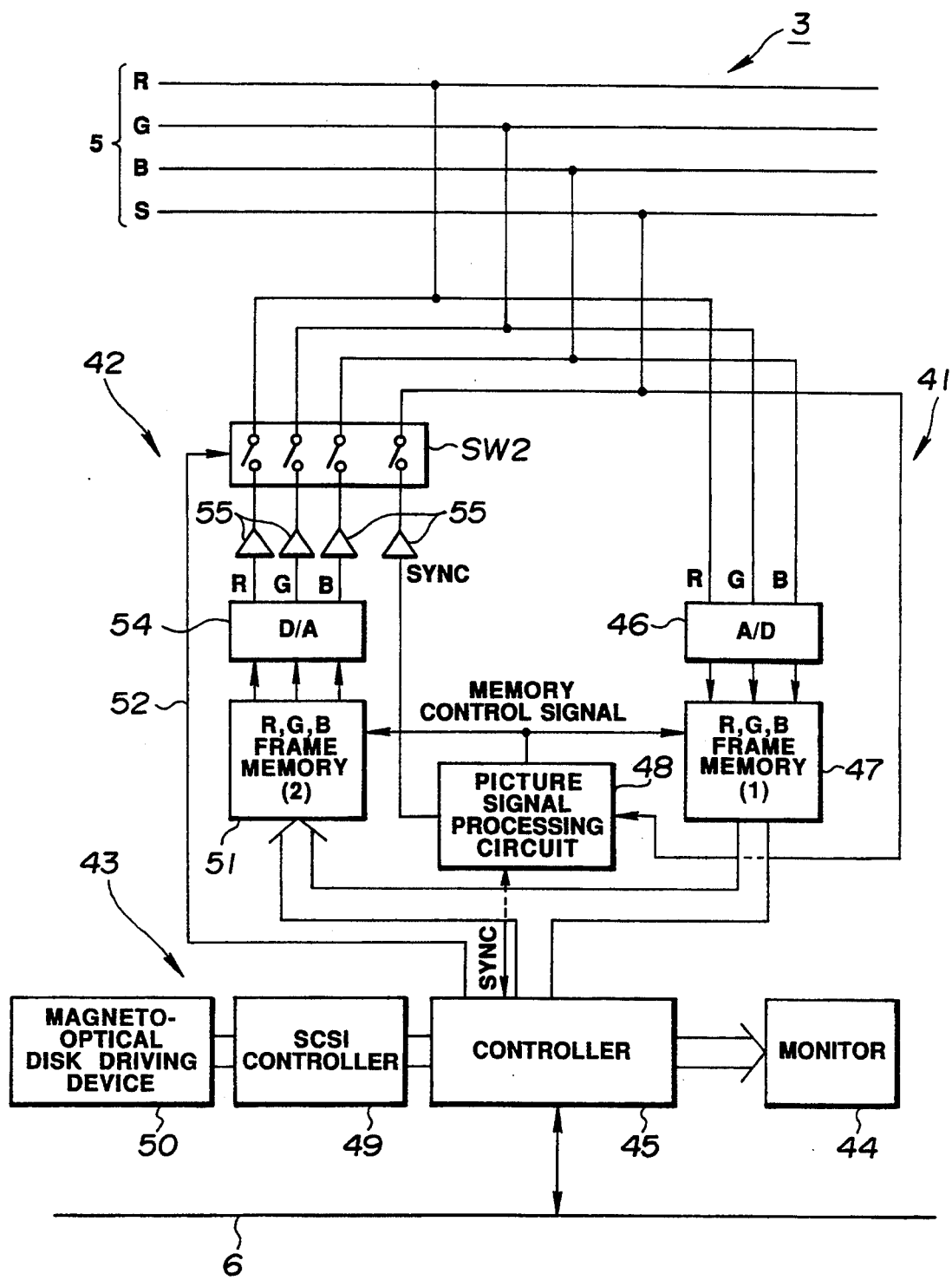

FIG. 4 shows the schematic construction of the centralized control system 3.

The system 3 is comprised of a receiving process system 41, a transmission process system 42, a record-/reproduction system 43, a display monitor 44 and a controller 45. In other words, the R, G and B lines of the analog transmission line 5 are connected to an R, G and B frame memory (1) 47 through an A/D converter 46, and the S line is connected to a picture signal processing circuit 48.

The R, G and B frame memory (1) 47 is connected through a bus to the controller 45 which is connected to the digital transmission line 6 and to a magneto-optical disk driving device 50 for recording image information through an SCSI controller 49. After receiving, for example, a control signal to demand the registration of a static image from the electron microscope system (1) 2A or (2) 2B through the digital transmission line 6, the controller 45 sends a command indicating that transmission is available, and sets the receiving process system 41 on standby. When a synchronizing signal SYNC is sent through the S line of the analog transmission line 5, the picture signal processing circuit 48 detects the synchronizing signal SYNC, sends a memory control signal to the R, G and B frame memory (1) 47, and writes digital R, G and B signals in the frame memory (1) 47 through the A/D converter 46 in synchronization with the synchronizing signal SYNC.

When writing of endoscopic image information for one plane in the frame memory (1) 47 is completed, the image information in the frame memory (1) 47 is transferred to the controller 45, correlated with patient data sent through the digital transmission line 6, registered in, for example, a data base in the controller 45, and sent out to the magneto-optical disk driving device 50 through the SCSI controller 49, thereby registering a static image.

When accepting a retrieval request from the conference system (1) 4A or (2) 4B, the controller 45 retrieves in the data base and performs a control operation to read applicable image information registered in the magneto-optical disk driving device 50.

The image information read from the magneto-optical disk driving device 50 can be transferred to the controller 45 through the SCSI controller 49. Then, the controller 45 transfers digital R, G and B signals corresponding to the image information to an R, G and B frame memory (2) 51 through a bus.

Furthermore, the controller 45 turns on an analog switch SW2 through an analog transmission line transmission control signal line 52. The picture signal processing circuit 48 sends a memory control signal to the frame memory (2) 51 so as to output R, G and B signals in synchronization with the synchronizing signal SYNC generated by the picture signal processing circuit 48. The R, G and B signals read from the frame memory (2) 51 are converted into analog R, G and B signals by a D/A converter 54, and sent to the analog transmission line 5 together with the synchronizing signal SYNC through buffers 55 and the analog switch SW2 in synchronization.

Figure 5:
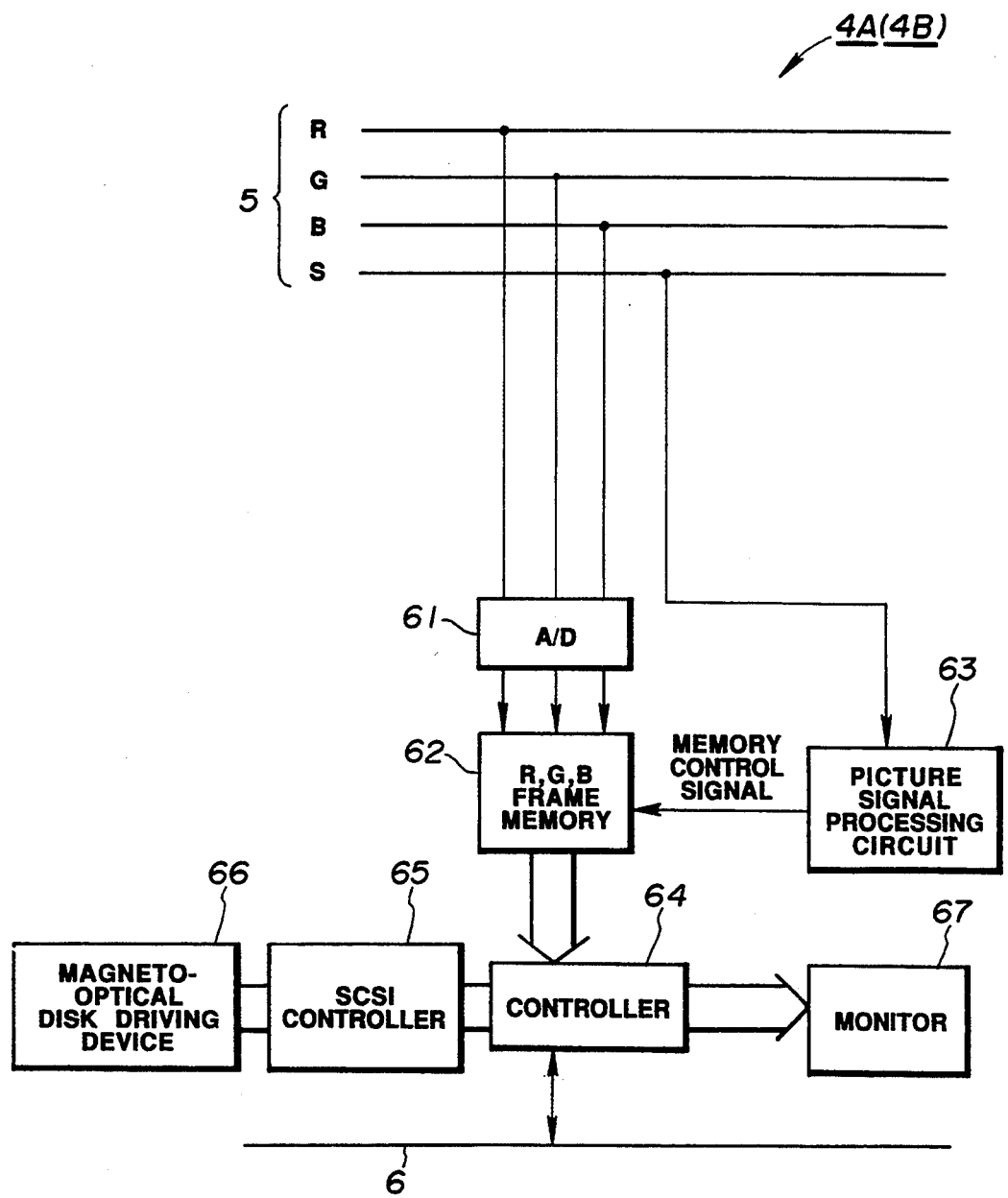

The construction of the conference system (1) 4A or (2) 4B is shown in FIG. 5.

The R, G and B lines of the analog transmission line 5 are connected to an A/D converter 61 so as to convert analog R, G and B signals into digital R, G and b signals and write the digital R, G and B signals in an R, G and B frame memory 62. The S line is connected to a picture signal processing circuit 63 so as to output a memory control signal in synchronization with an input synchronizing signal SYNC to the R, G and B frame memory 62 and output R, G and B signals in synchronization with the synchronizing signal SYNC. The R, G and B signals are transferred to a controller 64 and recorded as image information corresponding to patient data in a magneto-optical disk driving device 66 through an SCSI controller 65. Furthermore, the controller 64 can display the received signals or signals reproduced from the magneto-optical disk driving device 66 in a monitor 67.

A typical operation of the endoscopic image network system according to the first embodiment having such a construction will now be described.

(a) For example, an operation in which the electron microscope system (1) 2A registers a static image in the centralized control system 3 will be first described.

(1) The electron microscope system (1) 2A sends a command for demanding to obtain a transmission right of the analog transmission line 5 to the centralized control system 3 by using the digital transmission line 6, and a command indicating that the centralized control system 3 performs receiving.

(2) Then, the controller 45 of the centralized control system 3 receives the command in (1), and checks whether or not the analog transmission line 5 is being used by other systems at present. If the analog transmission line 5 is not being used, the controller 45 sends a reply command to permit transmission to the electron microscope system (1) 2A. (Whether the analog transmission line 5 is used is determined based on whether a synchronizing signal SYNC of the S line is present in the picture signal processing circuit 48.) At this time, the centralized control system 3 stands by in readiness for taking an image into the frame memory (1) 47 in synchronization with the synchronizing signal SYNC.

(3) When receiving the command to permit transmission in (2), the electron microscope system (1) 2A turns on the analog switch SW1 by using the analog transmission line transmission control signal line 9, transmits R, G and B signals as image information through the analog transmission line 5, and transmits patient information corresponding to the R, G and B signals by using the digital transmission line 6.

(4) The centralized control system 3 takes the R, G and B signals transmitted from the electron microscope system (1) 2A through the analog transmission line 5 into the R, G and B frame memory (1) 47 in synchronization with the SYNC signal.

Subsequently, based on the patient information transmitted through the digital transmission line 6, the number of the information and so on are registered in an endoscopic information data base managed by the centralized control system 3, and the image information is recorded onto a magneto-optical disk which is set on the magneto-optical disk driving device 50 through the SCSI controller 49.

(5) According to the above operation (4), all the image information from the electron microscope system (1) 2A is registered in the data base of the centralized control system 3.

(b) Next, the case in which the image is reproduced on the monitor 67 of the conference system (1) 4A for diagnosis will be described.

(6) The conference system (1) 4A sends information (ID No, name and so on) on a patient to be examined to the centralized control system 3 by using the digital transmission line 6.

(7) The centralized control system 3 starts retrieval based on the transmitted patient information by using the data base.

(8) When the retrieval reveals that the patient is registered, an image relative to the patient is read from the magneto-optical disk driving device 50 and stored in the R, G and B frame memory (2) 51.

(9) The controller 45 of the centralized control system 3 checks whether or not the analog transmission line 5 is in an empty state. If another system is using the analog transmission line 5 for image transmission/receiving, the controller 45 stands by until the use is finished. If the analog transmission line 5 is not being used, the next operation is carried out.

(10) The controller 45 of the centralized control system 3 transmits a command indicating that the applicable patient data has been found to the conference system (1) 4A, turns on the analog switch SW2, and transmits information in the R, G and B frame memory (2) 51 to the analog transmission line 5.

(11) The conference system (1) 4A takes the image information transmitted from the centralized control system 3 into the R, G and B frame memory 62.

(12) The image information taken in the R, G and B frame memory 62 is recorded on a magneto-optical disk set in the magneto-optical disk driving device 66 or displayed on the monitor 67 for diagnosis.

(c) Although the operations in which a static image is registered from the electron microscope system (1) 2A in the centralized control system 3 and in which the conference system (1) 4A retrieves an image from the centralized control system 3 are mentioned in the above (a) and (b), it is also possible to directly output the image of the electron microscope system (1) 2A or (2) 2B on the monitor 67 of the conference system (1) 4A or (2) 4B. In this case, the control operation is performed by the centralized control system 3.

For example, the conference system (1) 4A or (2) 4B can observe the examination by the electron microscope system (1) 2A or (2) 2B and give instructions to the electron microscope system (1) 2A or (2) 2B.

(d) Patient information, such as case data, additionally created when the conference system (1) 4A or 4B performs diagnosis can be reversely transmitted from the conference system (1) 4A or (2) 4B to the centralized control system 3 through the digital transmission line 6, and added to the data base of the centralized control system 3.

According to the first embodiment, since the endoscopic image information is transmitted through the analog transmission line 5, the transmission can be performed at high speed. Furthermore, since control signals and patient data are transmitted in two ways by using the digital transmission line 6 separate from the analog transmission line 5, the construction of the control system can be simplified and materialized at low cost.

Although the endoscopic image information is transmitted by the analog transmission line 5 in the above embodiment, there may be a demand to transmit an endoscopic image of an important case and so on without causing any deterioration of the image, even if the transmission takes much time. In such a case, it is possible to transmit the important image by using the digital transmission line which is used for transmission of patient data and the like.

In short,
(1) The analog transmission line capable of achieving high speed transmission is used to transmit an ordinary image; and
(2) The digital transmission line capable of performing transmission without causing any deterioration is used to transmit an important image.

Figure 6:
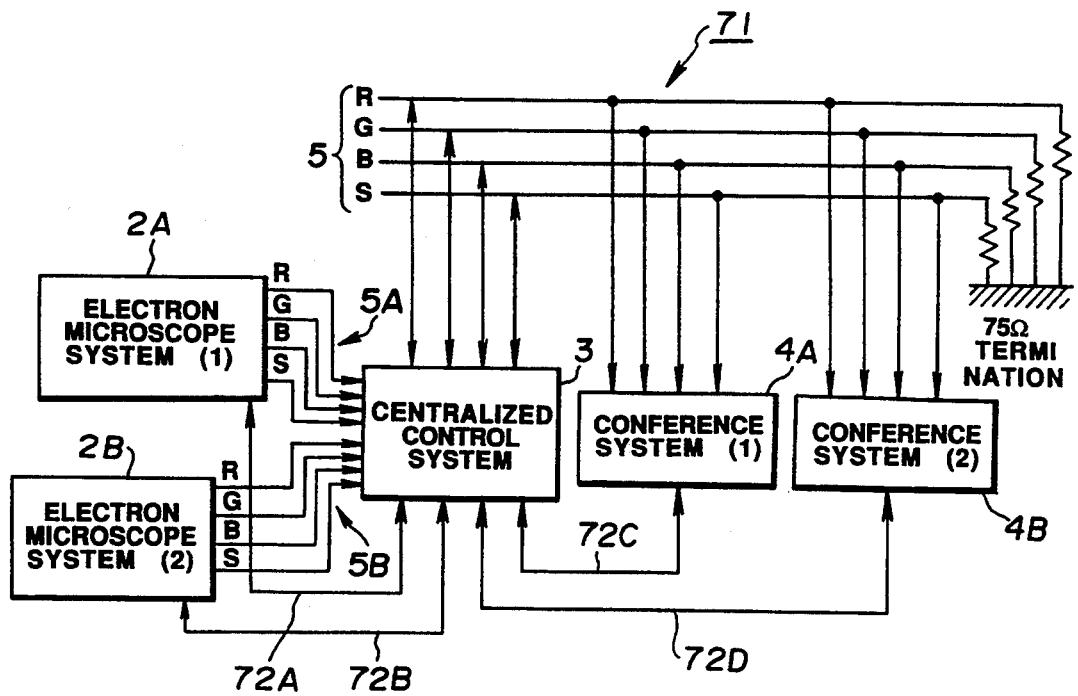
FIGS. 6 to 9 each show a second embodiment of the present invention.

FIG. 6 schematically shows the construction of an endoscopic image network system 71 according to a second embodiment of the present invention.

In the second embodiment, RS-232C lines are used as digital transmission means.

Electron microscope systems (1) 2A and (2) 2B are connected to a centralized control system 3 through RS-232C digital transmission lines 72A and 72B, respectively, and conference systems (1) 4A and (2) 4B are connected to the centralized control system 3 through RS-232C digital transmission lines 72C and 72D.

The electron microscope systems (1) 2A and (2) 2B are also connected to the centralized control system 3 through exclusive analog transmission lines 5A and 5B, each composed of R, G, B and S lines, respectively. On the other hand, the conference systems (1) 4A and (2) 4B are connected to the centralized control system 3 through a common analog transmission line 5.

Figure 7:
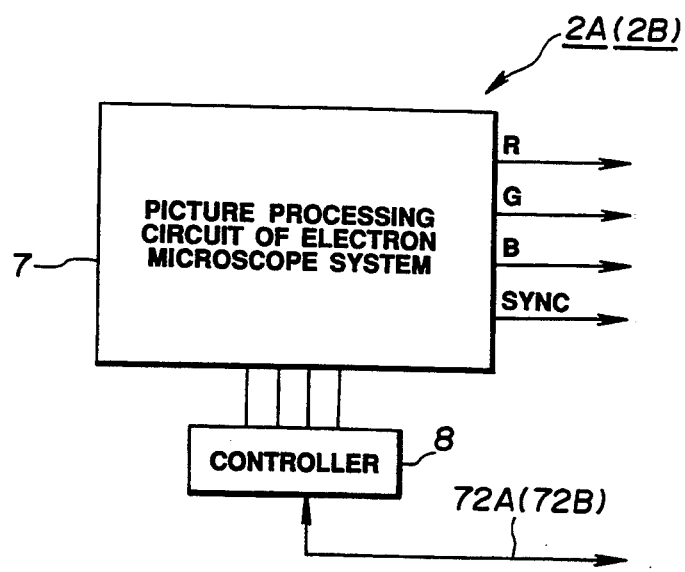

FIG. 7 shows the construction of the principal part of the electron microscope system (1) 2A or (2) 2B. In this embodiment, R, G, B and S signals are directly output to the centralized control system 3 through the analog transmission line 5A or 5B without using the analog switch SW1 shown in the first embodiment. Furthermore, a controller 8 is connected to the centralized control system 3 through the RS-232C digital transmission line 72A or 72B.

Figure 8:
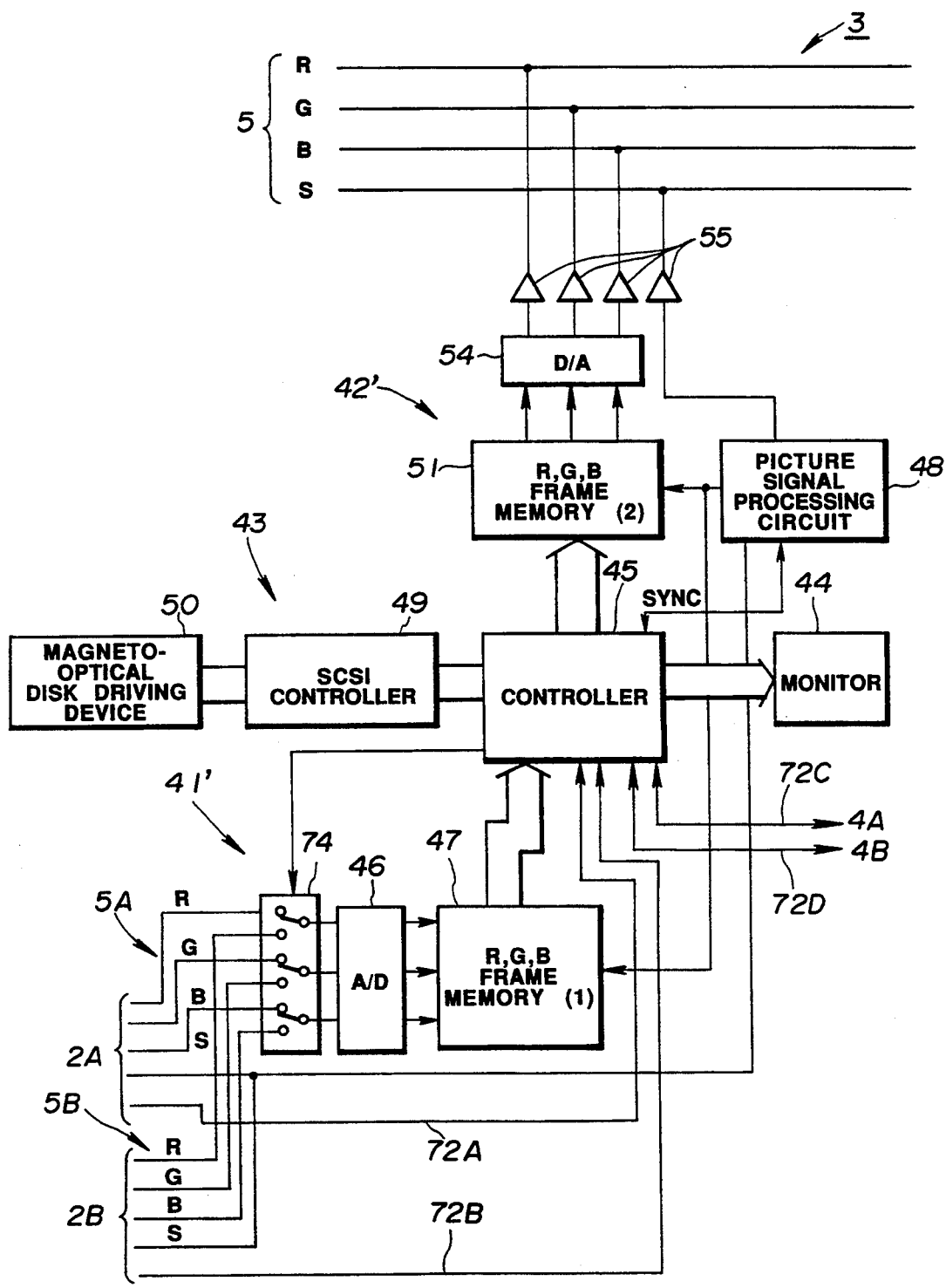

FIG. 8 schematically shows the construction of the centralized control system 3.

In this embodiment, a signal receiving process system 41' is different from the receiving process system 41 shown in FIG. 4 in that it is separated from the common analog transmission line 5 and connected to the analog transmission lines 5A and 5B connected to the electron microscope system (1) 2A and (2) 2B through a select switch 74 which is controlled by the controller 45.

A transmission process system 42' does not have the analog switch SW2 of the transmission process system 42 shown in FIG. 4, and outputs signals from a buffer 55 to the analog transmission line 5.

Furthermore, the controller 45 is connected to the systems 2A, 2B, 4A and 4B through the RS-232C digital transmission lines 72A, 72B, 72C and 72D. Although the lines of the electron microscope systems (1) 2A and (2) 2B are directly connected to a picture signal processing circuit 48 in FIG. 8, they may be connected through the switch 74. Other components are the same as those in the first embodiment, and denoted by like numerals.

Figure 9:
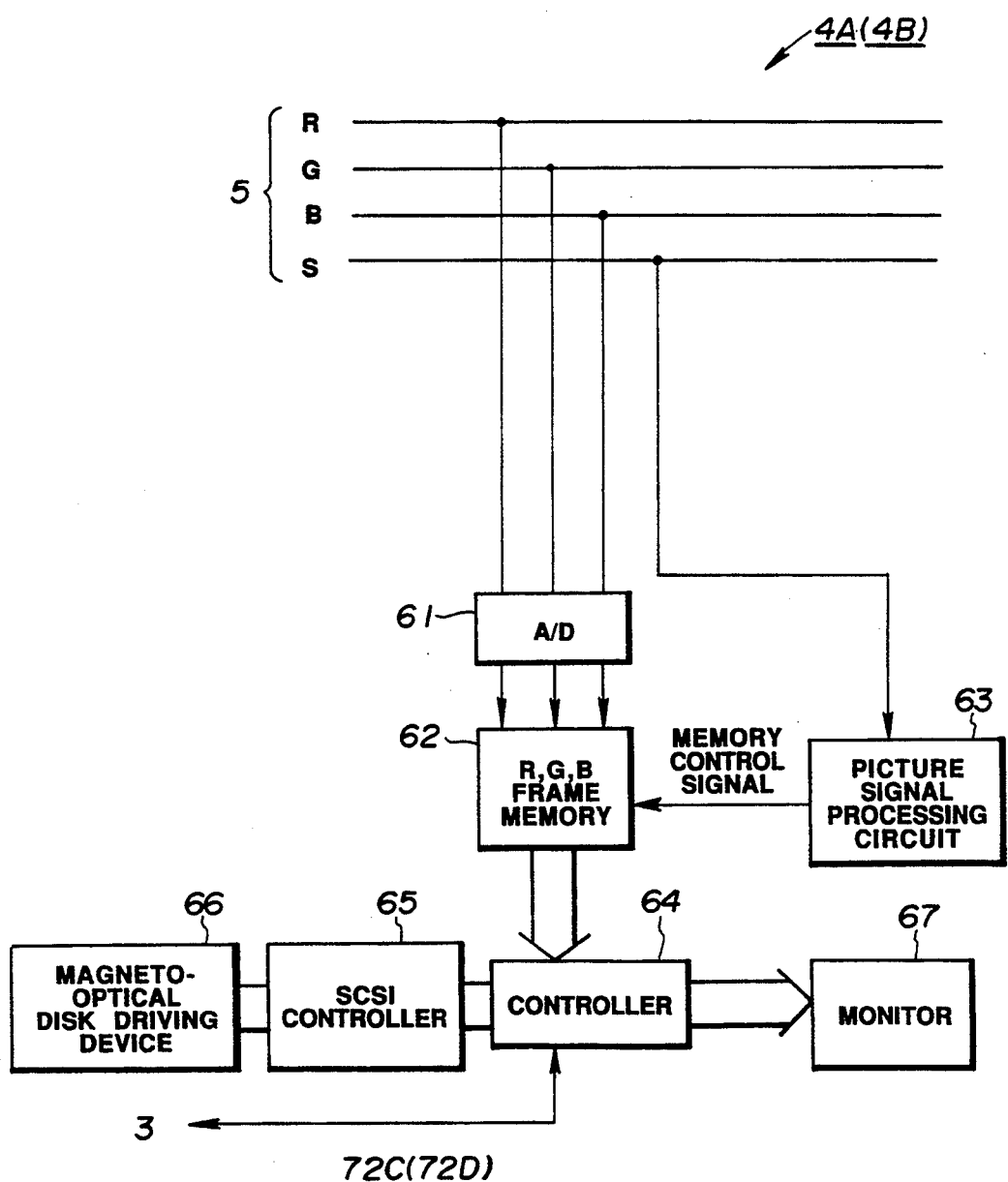

FIG. 9 schematically shows the conference system (1) 4A or (2) 4B.

The conference system (1) 4A or (2) 4B uses the RS-232C digital transmission line 72C or 72D instead of the digital transmission line 6 in the conference system (1) 4A or (2) 4B shown in FIG. 5. A controller 64 is connected to the controller 45 of the centralized control system 3 through the digital transmission line 72C or 72D so as to transmit control signals and so on in two ways. Other components are the same as those shown in FIG. 5.

In the second embodiment, the controller 45 of the centralized control system 3 monitors commands for a transmission right or a receiving right transmitted from the RS-232C digital transmission lines 72A, 72B, 72C and 72D, and gives priority to one of the systems 2A, 2B, 4A and 4B which first transmits a command, and puts the other systems into a standby state.

On accepting image transmission from the electron microscope system (1) 2A or (2) 2B, the controller 45 outputs a select signal to select the analog transmission line 5A or 5B connected to the electron microscope system (1) 2A or (2) 2B so as to control the select switch 74, sends a signal to permit the transmission, and stores image information in an R, G and B frame memory (1) 47 in synchronization with the SYNC signal.

Other operations are almost the same as those in the first embodiment. The second embodiment has almost the same advantages as those of the first embodiment, that is, of being capable of transmitting image information in a short time and so on. Furthermore, it is possible to make the digital transmission system more compact than that of the first embodiment, and thus to reduce costs.

Figure 10:
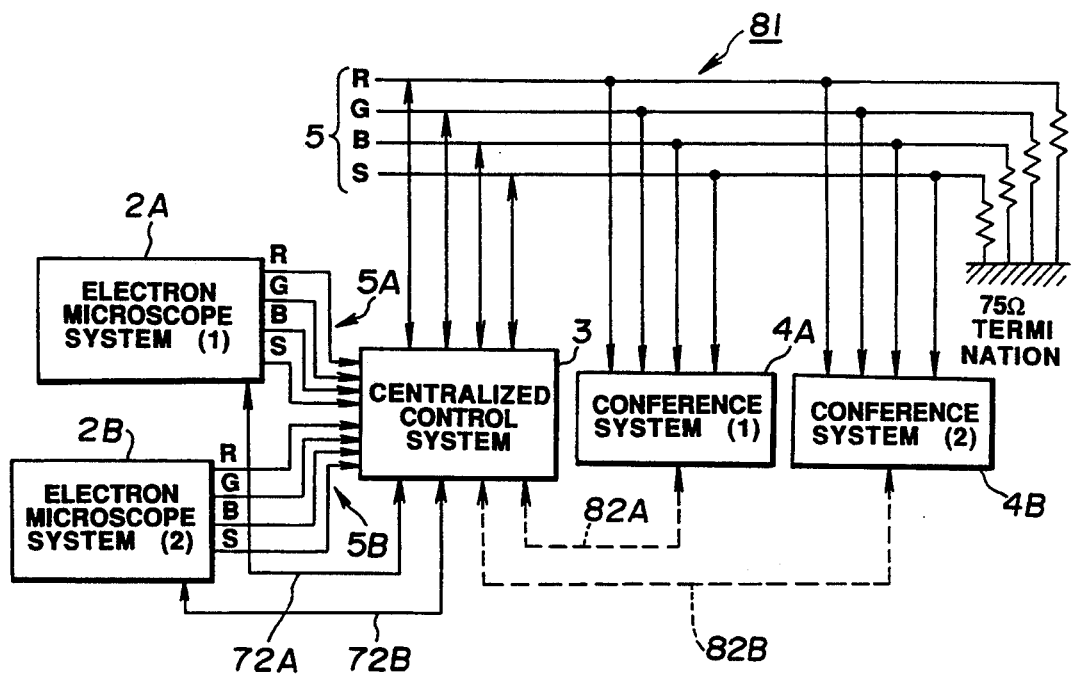

FIG. 10 schematically shows an endoscopic image network system 81 in a third embodiment of the present invention.

In the third embodiment, telephone lines 82A and 82B are used instead of the digital transmission lines 72C and 72D linking the centralized control system 3 and the conference systems (1) 4A and (2) 4B in the second embodiment shown in FIG. 6. Other components are the same as those in the second embodiment.

In a centralized control system 3 shown in FIG. 11, RS-232C digital transmission lines are connected to modems (1) 83A and (2) 83B, respectively, and the modems (1) 83A and (2) 83B are connected to the conference systems (1) 4A and (2) 4B through the telephone lines 82A and 82B, respectively. Other components are the same as those in FIG. 8. Furthermore, in the conference systems (1) 4A and (2) 4B shown in FIG. 12, an RS-232C digital transmission line is connected to a modem 85 which is connected to the modem 83A or 83B of the centralized control system 3 through the telephone line 82A (or 82B). Other components are the same as those shown in FIG. 9.

Since the third embodiment uses telephone lines as digital transmission means between the centralized control system 3 and the conference systems (1) 4A and (2) 4B, it is not necessary to lay digital transmission lines between the above systems (3 and 4A, and 3 and 4B). Therefore, costs can be made lower than those of the second embodiment.

Figure 13:
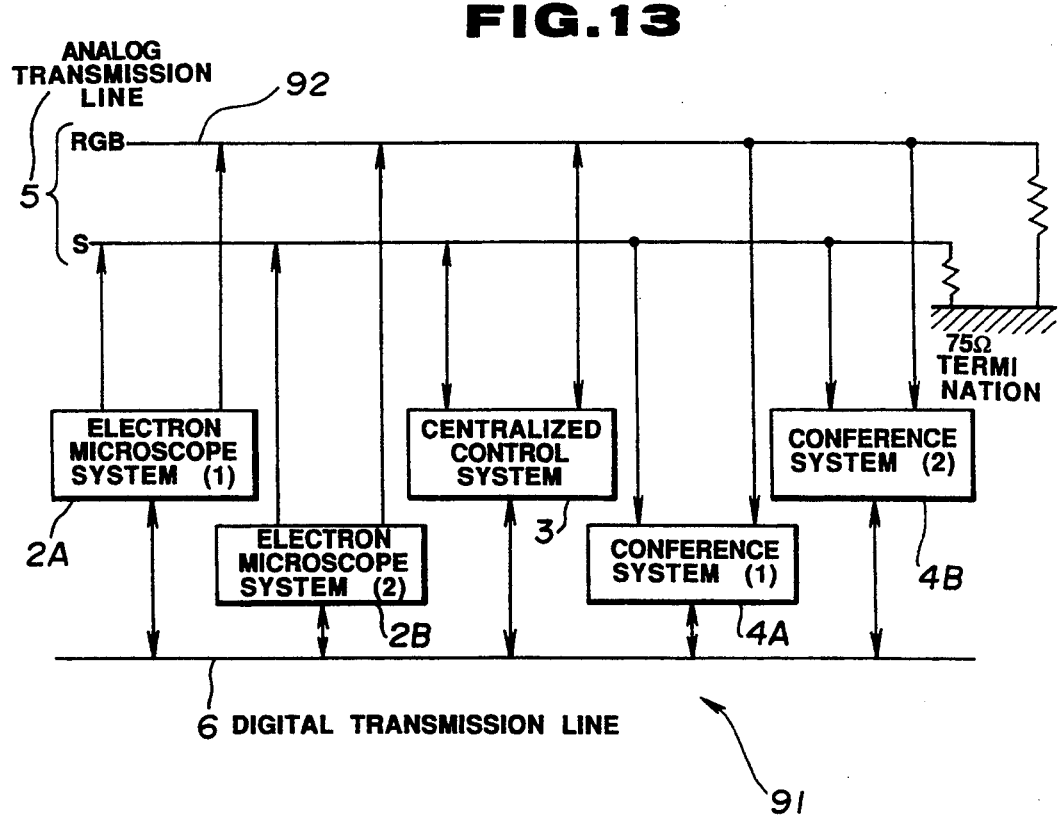

FIG. 13 shows a network system 91 according to a fourth embodiment of the present invention.

The system 91 serially and sequentially transmits R, G and B signals by using an RGB line 92 instead of the three R, G and B lines in the first embodiment shown in FIG. 1. Therefore, an analog transmission line 5' in this embodiment is composed of two coaxial cables, that is, the RGB line 92 and an S line.

As shown in FIG. 14a, the R, G and B signals each are sequentially transmitted to the RGB line 92 in separate even and odd fields in synchronization with an SYNC signal in the S line shown in FIG. 14b. In order to distinguish starts of the even and odd fields in each frame, for example, the SYNC signal at the start of the even field is set longer than at the start of the odd field.

The principal part of the electron microscope system (1) 2A or (2) 2B in this embodiment is shown in FIG. 15.

The electron microscope system (1) 2A or (2) 2B has a select switch 93 for switching R, G and B outputs and an analog switch 94 having two circuits for simultaneously turning on/off the output of the select switch 93 and the SYNC output instead of the analog switch SW1 in the first embodiment shown in FIG. 2,. The controller 8 controls switching/closing of the select switch 93 and the analog switch 94 through an RGB switch signal line 95 and the analog transmission line transmission control signal line 9, respectively.

Figure 16:
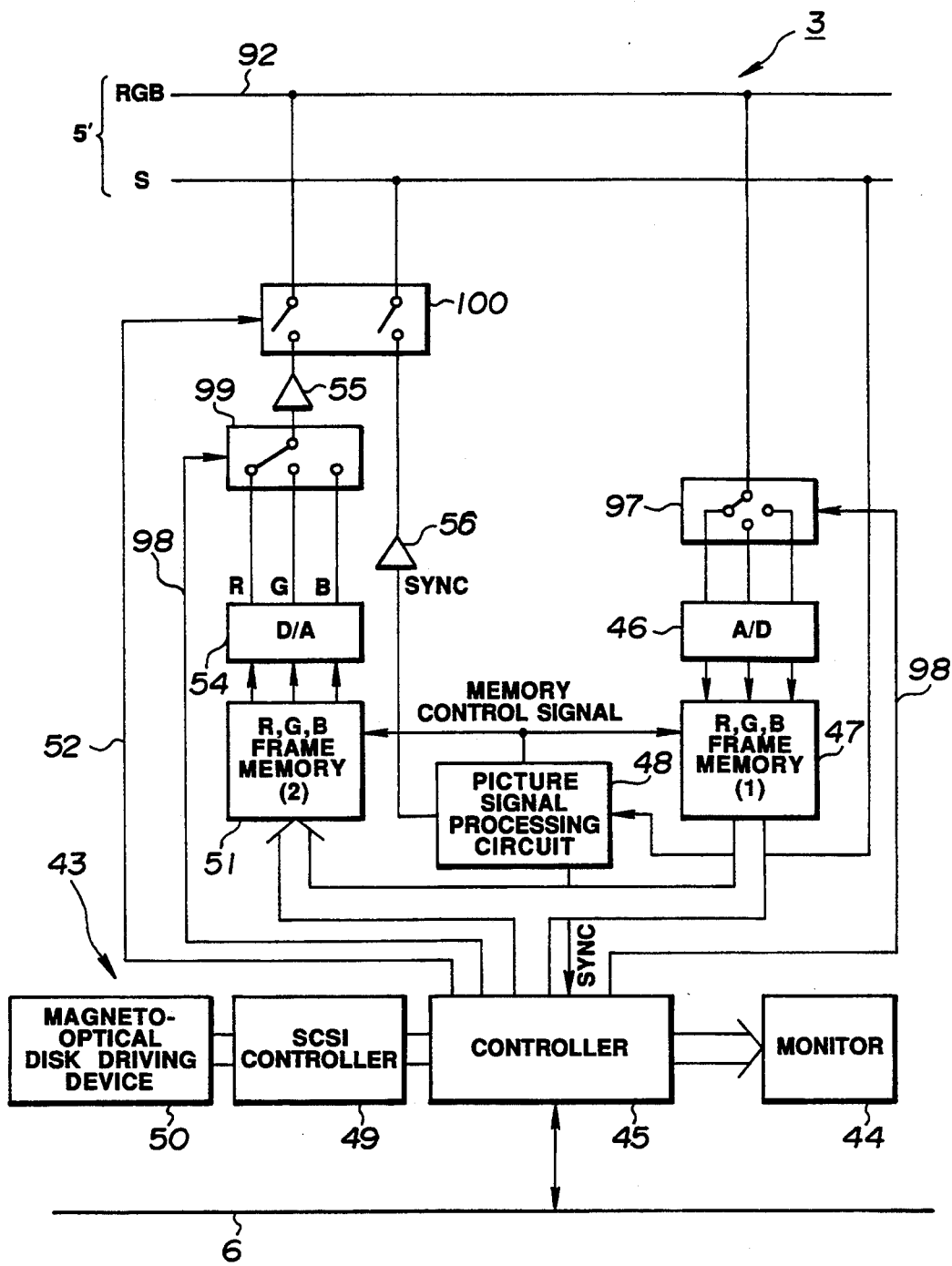

In a centralized control system 3 shown in FIG. 16, a select switch 97 is mounted at an input terminal of an A/D converter 46, which is the same as the A/D converter 46 in the first embodiment shown in FIG. 4, in the signal receiving process system 41 so as to be in connection with the RGB line 92, and actuated by a controller 45 through an RGB switch signal line 98.

R, G and B outputs of a D/A converter 54, which is the same as the D/A converter 54 in the transmission process system 42 shown in FIG. 4, are input to a common buffer 55 through a select switch 99 having three contacts. The output of this buffer 55 and the output of a buffer 56 to which a SYNC signal is input can be supplied to the RGB line 92 and the S line through an analog switch 100 having two circuits, respectively.

The opening and closing of the analog switch 100 are controlled by the controller 45 through an analog transmission line transmission control signal line 52. Other components are the same as those shown in FIG. 4.

Figure 17:
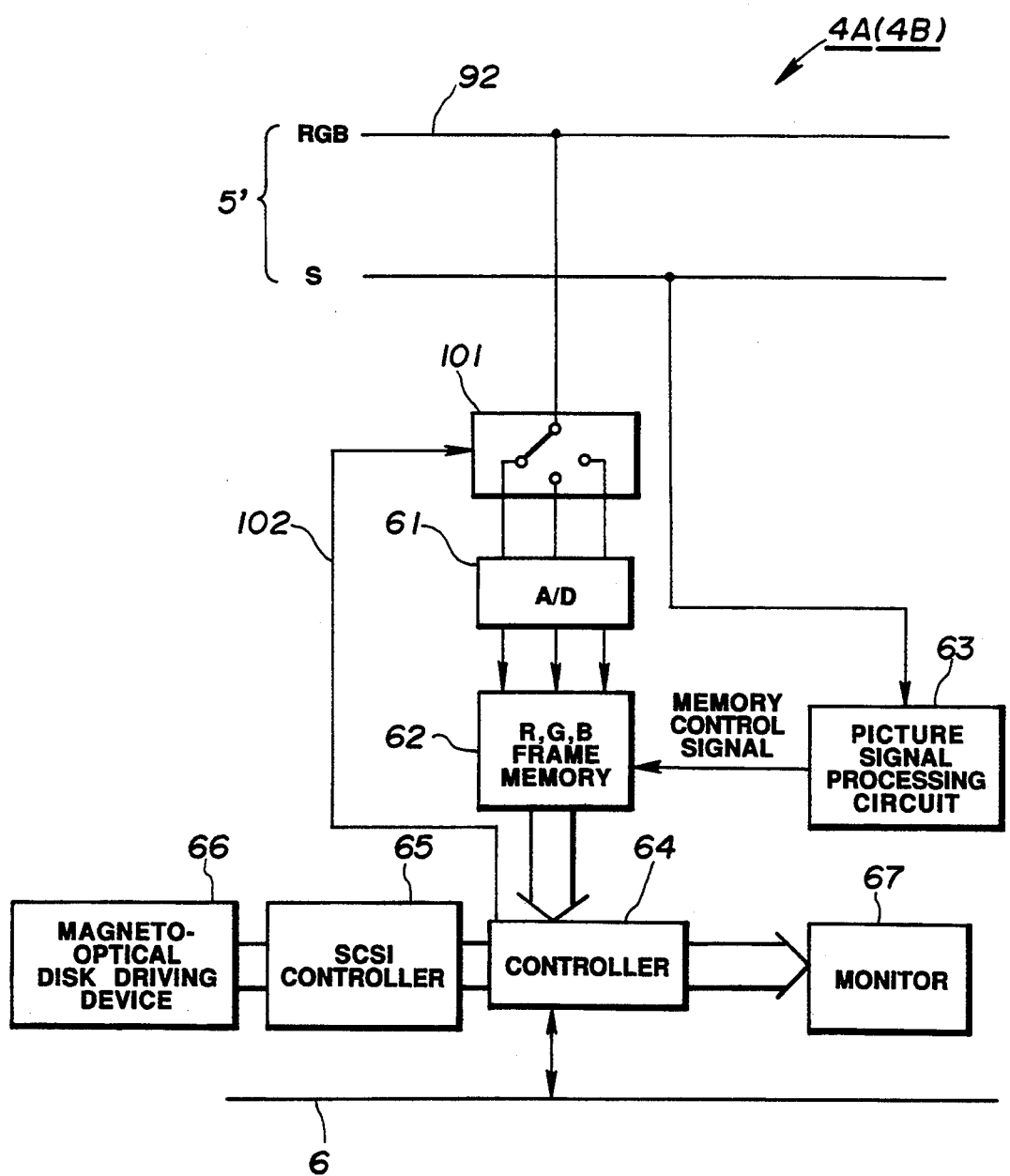

In the conference system (1) 4A or (2) 4B shown in FIG. 17, a select switch 101 is disposed at a stage previous to an A/D converter 61, which is the same as the A/D converter 61 shown in FIG. 5, and connected to the RGB line 92. The select switch 101 is controlled by a controller 64 through an RGB select signal line 102. Other components are the same as those shown in FIG. 5.

The fourth embodiment can combine the R, G and B lines in the first embodiment into a single line, and thus reduce the costs of laying some lines.

A fifth embodiment of the present invention will now be described. Although two lines, that is, the RGB transmission line and the SYNC transmission line are necessary as analog transmission lines in the above fourth embodiment, an analog transmission line 5'' in this embodiment is composed of only an RGBS signal transmission line 92 by superimposing an SYNC signal on the RGB signal line in the fourth embodiment.

Figure 18:
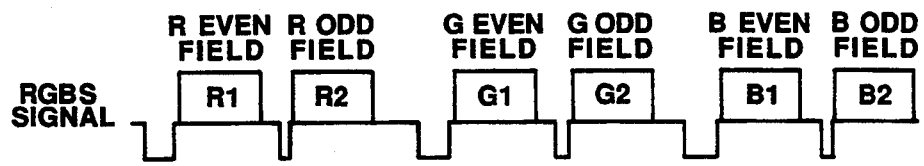
FIGS. 18 to 21 each show a fifth embodiment of the present invention.

The form of an RGBS signal shown in FIG. 18 is obtained by superimposing the two signals shown in FIGS. 14a and 14b.

Figure 19:
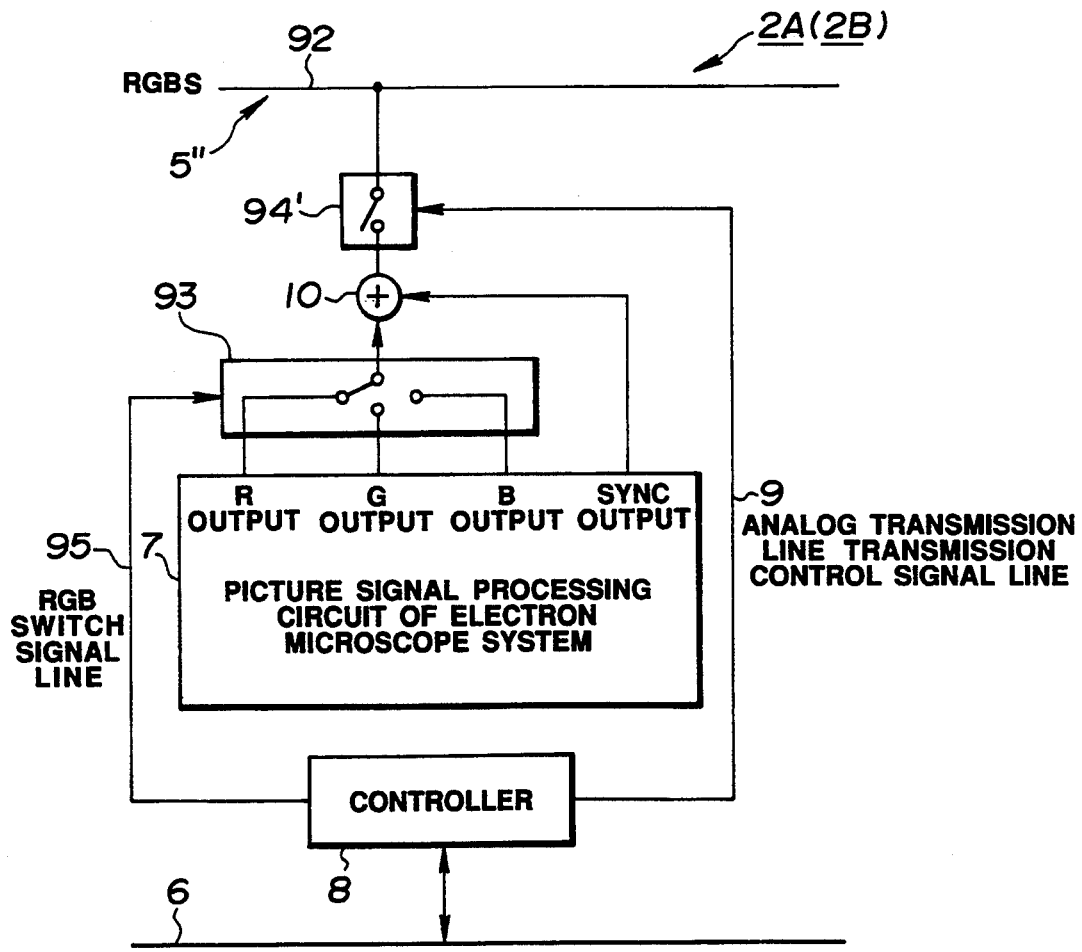

FIG. 19 shows an electron microscope system (1) 2A or (2) 2B in the fifth embodiment. The electron microscope system (1) 2A or (2) 2B does not have the SYNC signal line shown in FIG. 15. Furthermore, one of switch portions of the switch 94 connected to the SYNC signal line is omitted, and only a switch 94' connected to the analog transmission line 92 for transmitting an RGBS signal is only disposed instead. An SYNC signal output from an SYNC output terminal of a picture signal processing circuit 7 of the electron microscope system (1) 2A or (2) 2B is added to the output of a switch 93 by an adder 10. Other components are the same as those in FIG. 15.

Figure 20:
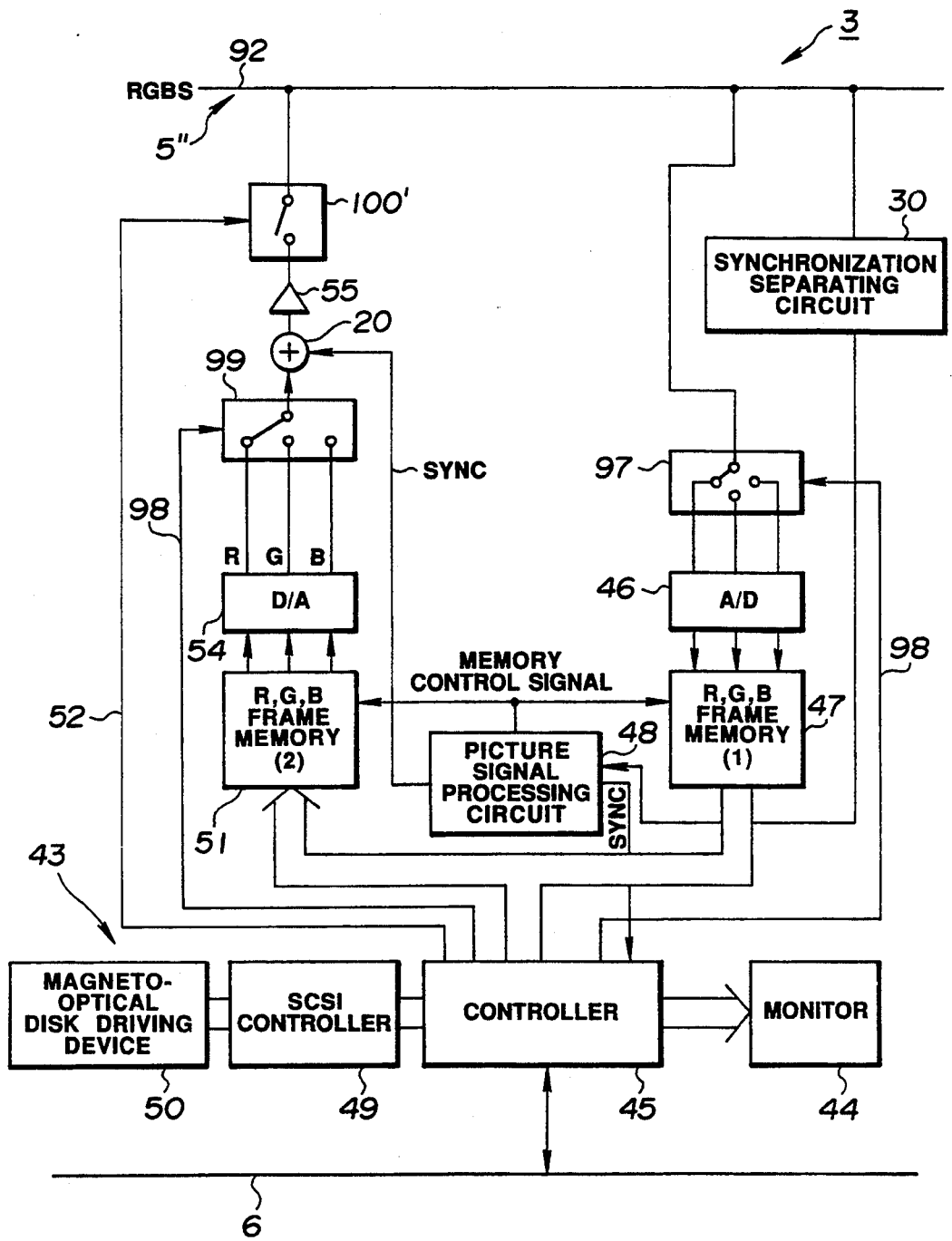

A centralized control system 3 in this embodiment is shown in FIG. 20. The centralized control system 3 does not have the SYNC signal line shown in FIG. 16. Furthermore, one of switch portions of the switch 100 connected to the SYNC signal line is omitted, and only a switch 100' connected to the analog transmission line 92 for transmitting an RGBS signal is disposed instead. An SYNC signal output from a picture signal processing circuit 48 of the electron microscope system (1) 2A or (2) 2B is added to the output of a switch 99 by an adder 20, and then output to the analog transmission line 92 through a buffer 55 and the switch 100'.

Although the SYNC signal is directly input to the picture signal processing circuit 48 in FIG. 16, the SYNC signal in this fifth embodiment is separated by an synchronization separating circuit 30 and input to the picture signal processing circuit 48. Other components are the same as those shown in FIG. 16.

Figure 21:
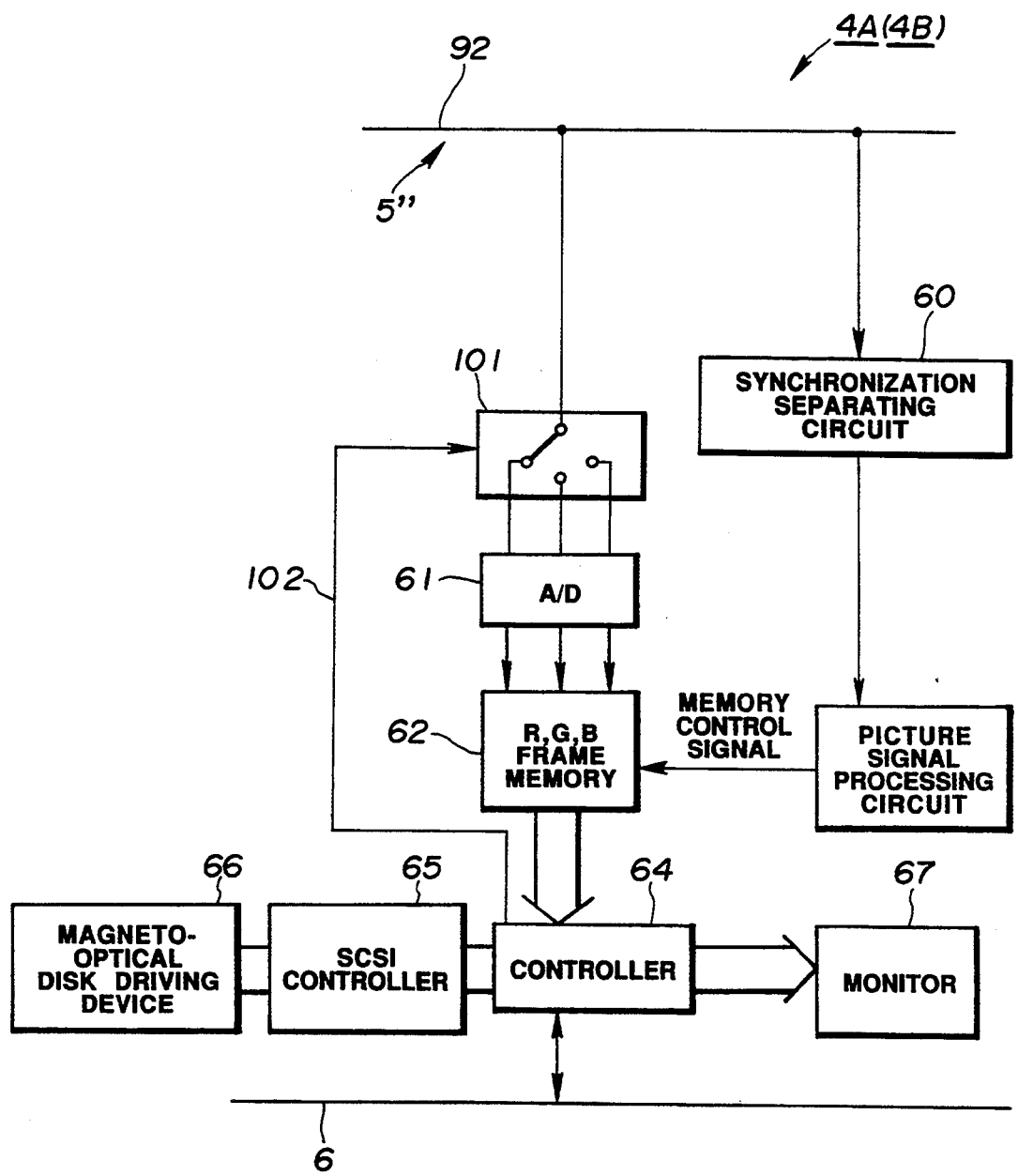

FIG. 21 shows a conference system 4A or 4B in the fifth embodiment. The conference system 4A or 4B does not have the SYNC signal line shown in FIG. 17. Furthermore, although the SYNC signal is directly input to the picture signal processing circuit 63 in FIG. 17, the SYNC signal in this embodiment is separated by an synchronization separating circuit 60 and input to a picture signal processing circuit 63. Other components are the same as those shown in FIG. 17.

According to this embodiment, since only the single analog transmission line 5'' is necessary, it is possible to further reduce the costs of laying some lines and so on.

A sixth embodiment of the present invention will now be described. The above fourth embodiment needs three transmission lines, that is, one RGB transmission line and one SYNC signal transmission line as analog transmission lines and one digital transmission line. The sixth embodiment makes it possible to transmit signals through two transmission lines by superimposing an SYNC signal on a digital transmission line.

Figure 22A:
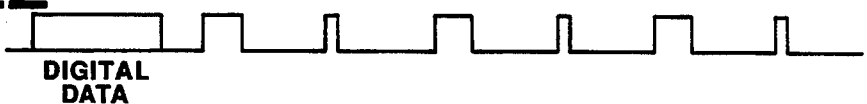
FIGS. 22 to 25 each show a sixth embodiment of the present invention.
Figures 22B, 23:
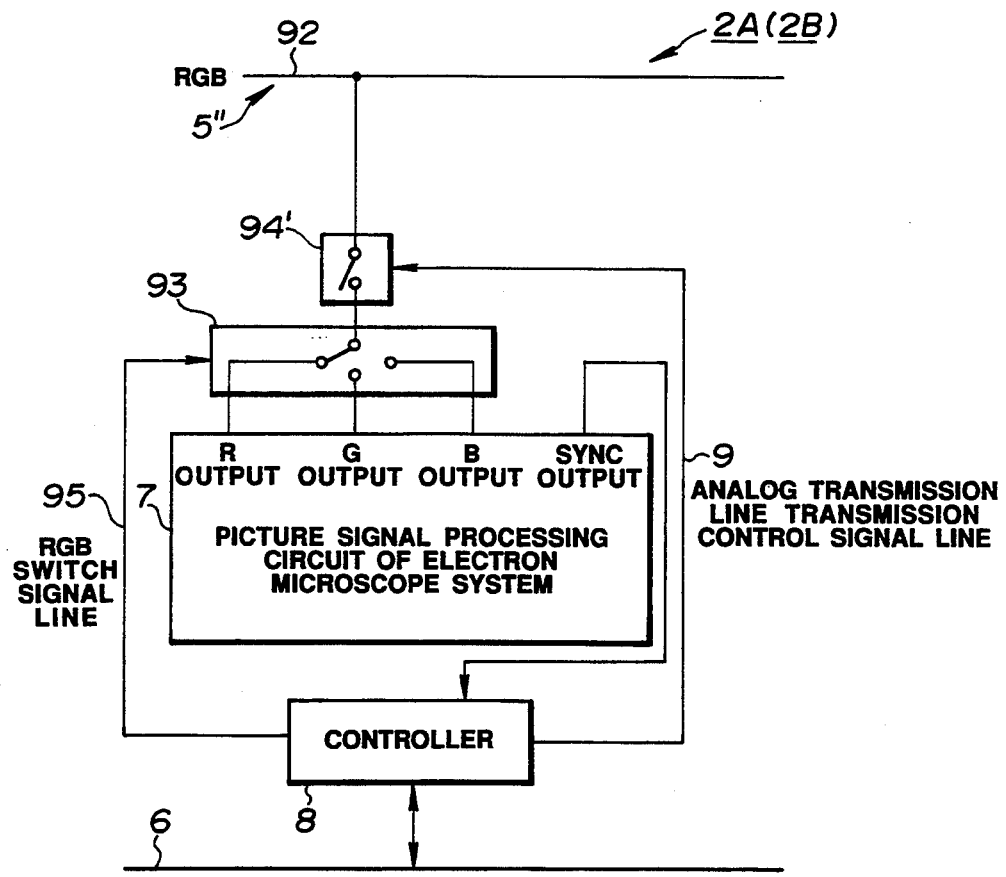

FIG. 22 shows forms of signals in this embodiment. The signal form of an RGB transmission line shown in FIG. 22a is the same as that in FIG. 14a. Furthermore, digital data, such as patient data, is superimposed on an SYNC signal, which is the same as the SYNC signal in FIG. 14, in an SYNC signal and digital signal line shown in FIG. 22b. The SYNC signal shown in 22b has a positive polarity.

FIG. 23 shows an electron microscope system (1) 2A or 92) 2B in this embodiment. The electron microscope system (1) 2A or (2) 2B does not have the SYNC signal line shown in FIG. 15. Furthermore, one of switch portions of the switch 94 connected to the SYNC signal line is omitted, and only a switch 94' connected to an analog transmission line 92 for transmitting R, G, B and S signals is disposed instead. An SYNC signal output from an SYNC output terminal of a picture signal processing circuit 7 of the electron microscope system (1) 2A or (2) 2B is input to a controller 8, which outputs the SYNC signal to a digital transmission line 6. Other components are the same as those in FIG. 15.

Figure 24:
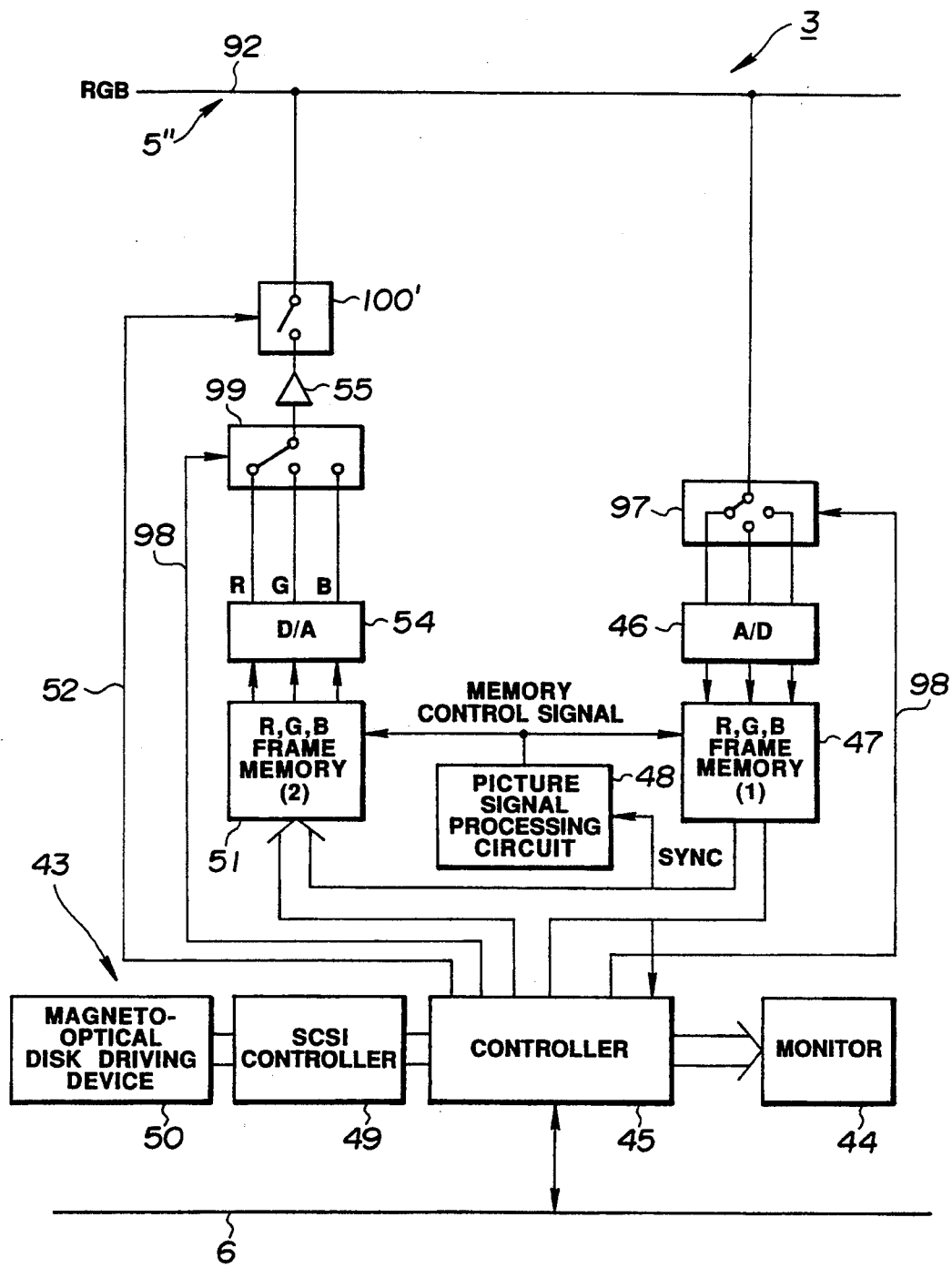

A centralized control system 3 in this embodiment is shown in FIG. 24. The centralized control system 3 does not have the SYNC signal line shown in FIG. 16. Furthermore, one of switch portions of the switch 100 connected to the SYNC signal line is omitted, and only a switch 100' connected to the analog transmission line 92 for transmitting R, G, B and S signals is disposed instead. An SYNC signal output from a picture signal processing circuit 48 is input to a controller 45, which outputs the SYNC signal to the digital transmission line 6.

The SYNC signal transmitted through the digital transmission line 6 is input to the controller 45 and output to the picture signal processing circuit 48.

When an image is sent from a frame memory (2) 51, the controller 45 receives an SYNC signal from the picture signal processing circuit 48, and transmits the SYNC signal to the digital transmission line 6. On the other hand, when an image is received by a frame memory (1) 47, the controller 45 receives an SYNC signal from the digital transmission line 6, and transmits the SYNC signal to the picture signal processing circuit 48. The picture signal processing circuit 48 takes, in synchronization with the received SYNC signal, an RGB image signal transmitted through the analog transmission line 92 into the frame memory (1) 47. Other components are the same as those shown in FIG. 16.

Figure 25:
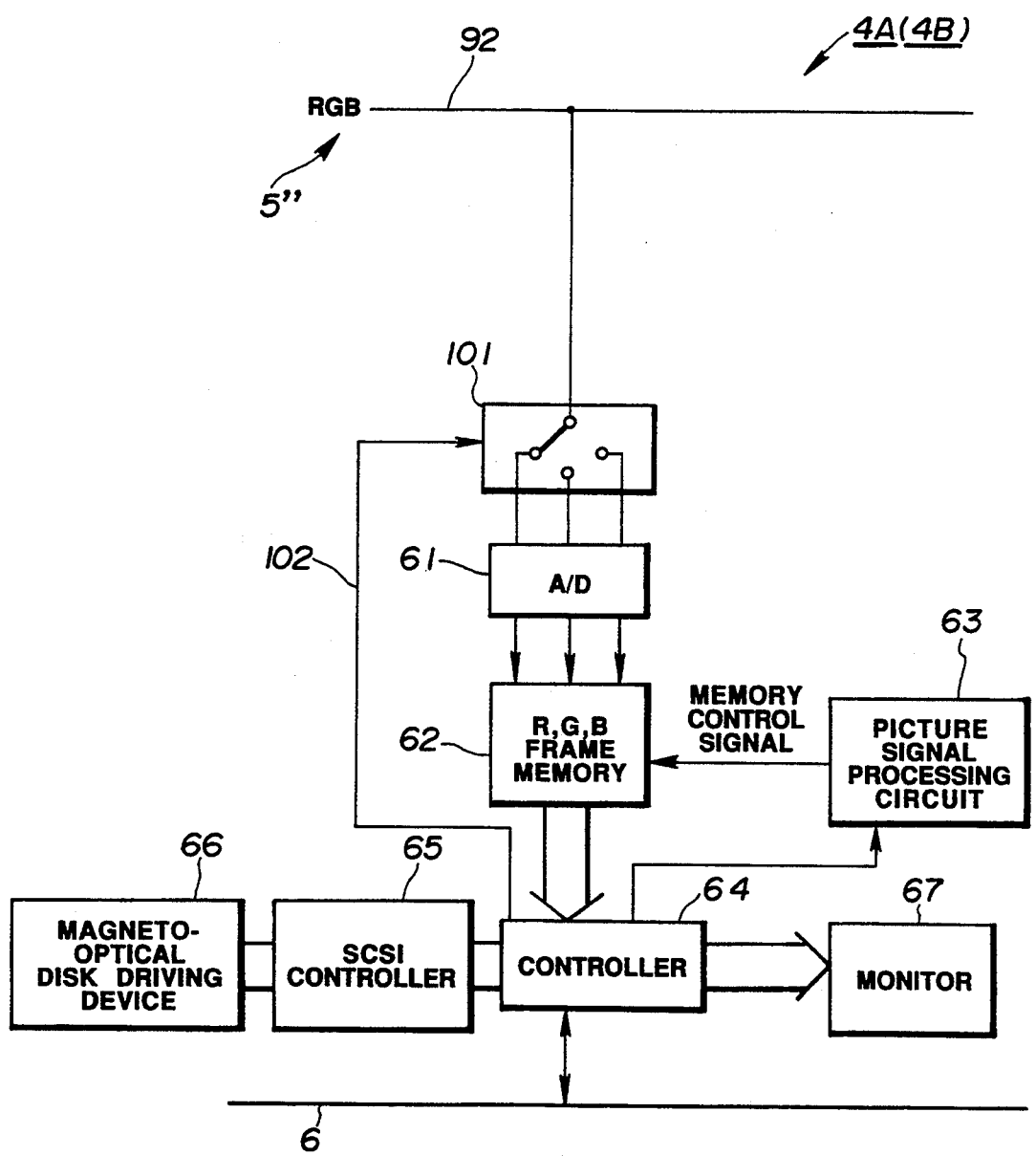

FIG. 25 shows a conference system 4A or 4B in the sixth embodiment. The conference system 4A or 4B does not have the SYNC signal line shown in FIG. 17. When an image is received by a frame memory 62, a controller 64 receives an SYNC signal from the digital transmission line 6, and transmits the SYNC signal to a picture signal processing circuit 63.

The picture signal processing circuit 63 takes, in synchronization with the received SYNC signal, R, G and B image signals transmitted through the analog transmission line 92 into the frame memory 62. Other components are the same as those shown in FIG. 17.

According to the sixth embodiment, since only the single analog transmission line 5" is necessary, it is possible to make the costs of laying some lines and so on lower than those of the fourth embodiment.

Figure 26:
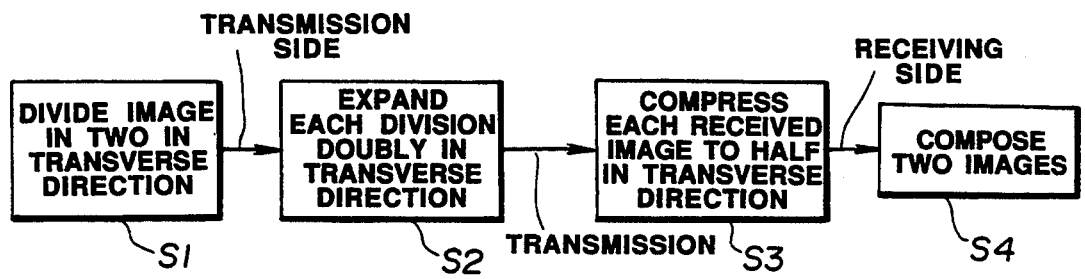
Figure 27:
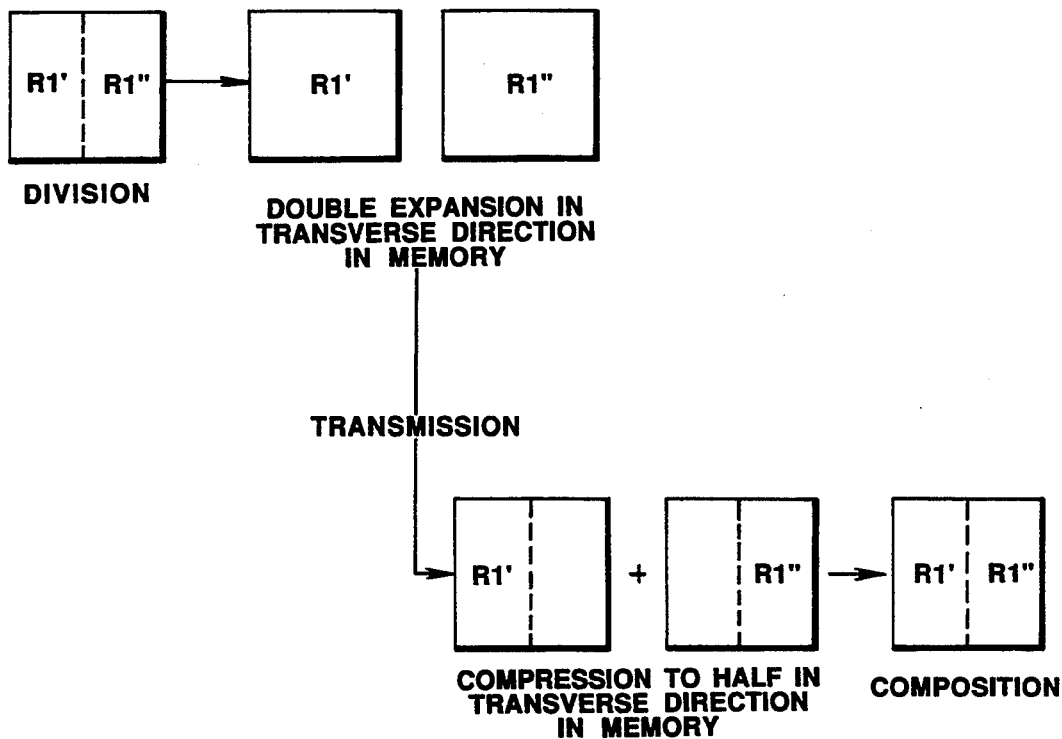

FIGS. 26 to 28 each explain a transmission method of R, G and B image information in a seventh embodiment of the present invention.

In the seventh embodiment, when an R, G and B signals are sent, a transmission side executes Step S1 of dividing an endoscopic image in two in the transverse direction as shown in FIG. 26, and then executes Step S2 of expanding the divided images doubly in the transverse direction so as to transmit the images. A receiving side executes Step S3 of compressing each received image to half in the transverse direction, and Step S4 of composing the two images into one.

FIG. 27 graphically shows the steps in FIG. 26. As shown in FIG. 27, for example, R1' and R1" are obtained by dividing one image having an R component in two in the transverse direction. Subsequently, the images R1' and R1" are doubly expanded in the transverse direction in a memory, and transmitted. The receiving side compresses the expanded images R1' and R1" to half in the transverse direction in the memory, and then composes the compressed images R1' and R1" into one image.

FIG. 28 shows image transmission using, for example, an R line according to this embodiment.

In other words, images R1' and R1" in an even field and images R2' and R2" in an odd field shown in FIG. 28a each are divided in two in synchronization with an SYNC signal shown in FIG. 28b, and transmitted.

According to the seventh embodiment, since transmission is performed while reducing a frequency band of a signal on the transmission side to half, even if some attenuation is caused in a high-frequency component due to the transmission line, deterioration of image information can be suppressed.

The seventh embodiment is applicable when an image is registered from the electron microscope systems (1) 2A or (2) 2B into the centralized control system 3, or when a retrieved image is sent from the centralized control system 3 to the conference system (1) 4A or (2) 4B. Furthermore, the seventh embodiment may be used in other embodiments.

FIG. 29 shows an image transmission method according to an eighth embodiment of the present invention.

In the transmission method of the fourth embodiment shown in FIG. 14 (FIGS. 29c and 29d which are the same as FIG. 14 are given in order to make a comparison plain), an image for one frame is transmitted by using six fields, that is, even and odd fields for each of an R component image, a G component image and a B component image. In the eighth embodiment, an image for one frame is transmitted by using only even fields for R and B component images, and even and odd fields for a G component image as shown in FIGS. 29a and 29b.

According to the eighth embodiment, since the amount of information to be transmitted can be reduced, the transmission of an image can be completed in a shorter time than in the above embodiments. The reason why the transmission amount can be reduced in this embodiment will be mentioned below.

In an endoscopic image, the amount of information in R and B component images is generally not so large. In other words, the R and B component images each have a little high-frequency component, and they are smooth images. On the other hand, the amount of information of a G component image is large. In short, the G component image includes minute information.

Therefore, as described above, the R and B component images are transmitted while being thinned out by one line in the longitudinal direction. Even if such R and B components are reproduced, there is little influence on diagnosis.

The transmission side or the receiving side may send a command to select a transmission method through the digital transmission line so as to change the transmission method to the method of the fourth or eighth embodiment in accordance with the select command.

Figure 30:
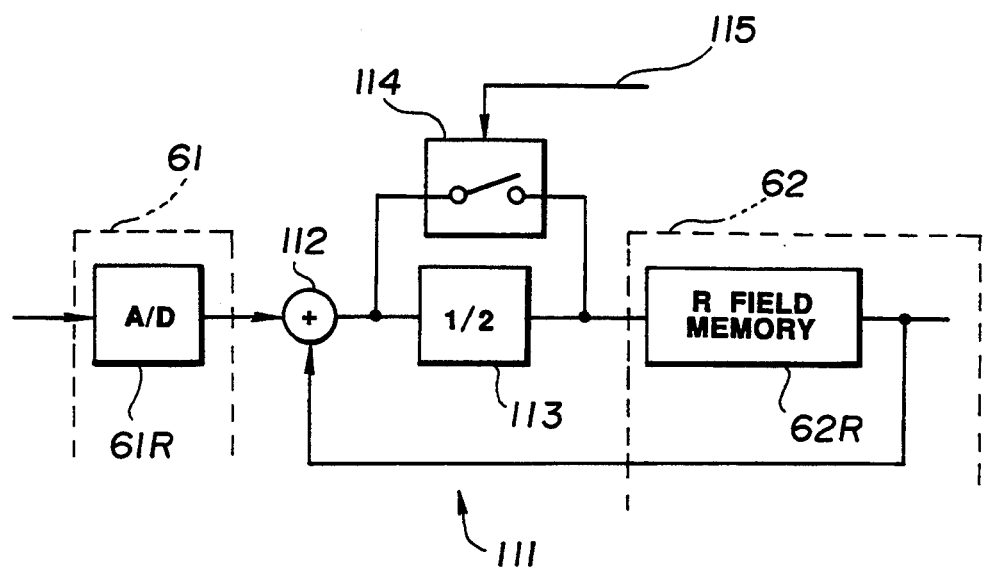
FIGS. 30 and 31 each show a ninth embodiment of the present invention.

FIG. 30 shows the principal part of a conference system (1) 4A or (2) 4B according to a ninth embodiment of the present invention.

In this embodiment, the same image is transmitted a plurality of times, and a plurality of transmitted images are added and averaged on the receiving side in order to reduce noise in a transmission system.

An output signal of an A/D converter 61R for an R component image as a component of, for example, the A/D converter 61 in the conference system (1) 4A or (2) 4B shown in FIG. 4 is input to a cyclic noise reducer 111.

In other words, the output signal of the A/D converter 61R is input to a ½ counter 113 through an adder 112, and to an R field memory 62R through a switch 114. The output of the R field memory 62R is input to the adder 112 and added to the output signal of the A/D converter 61R.

The opening and closing of the switch 114 are controlled by a controller 64 through a control signal line 115.

Figure 31:
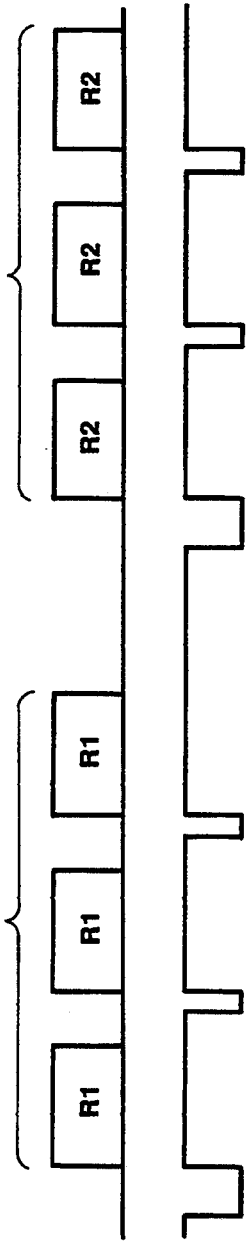

On the transmission side, an R signal sent by an R line shown in FIG. 31a transmits, for example, three images R1 in the same even field in synchronization with an SYNC signal shown in FIG. 31b, and then three images R2 in the same odd field.

On the receiving side, the controller 64 closes the switch 114 when the first image R1 is received, and stores the image R1 in the R field memory 62R.

In the case of the second image R1, the controller 64 opens the switch 114, simultaneously reads the first R1 which is stored in the R field memory 62R, adds the second image R1 to the first image R1 in the adder 112, halves the image by using the ½ counter 113, and stores the halved image in the R field memory 62R.

The same process as that for the second image R1 is performed for the third image R1, and a resultant image is stored in the R field memory 62R. After that, the image R1 stored in the R field memory 62R is stored in a magneto-optical disk in a magneto-optical disk driving device 66.

FIG. 31c explains the memory operation.

The same processes are conducted on the other R and B component images.

According to the ninth embodiment, it is possible to reduce noise in the transmission line.

Furthermore, this embodiment can be used when an image is registered from the electron microscope system (1) 2A or (2) 2B in the centralized control system 3.

Figure 32:
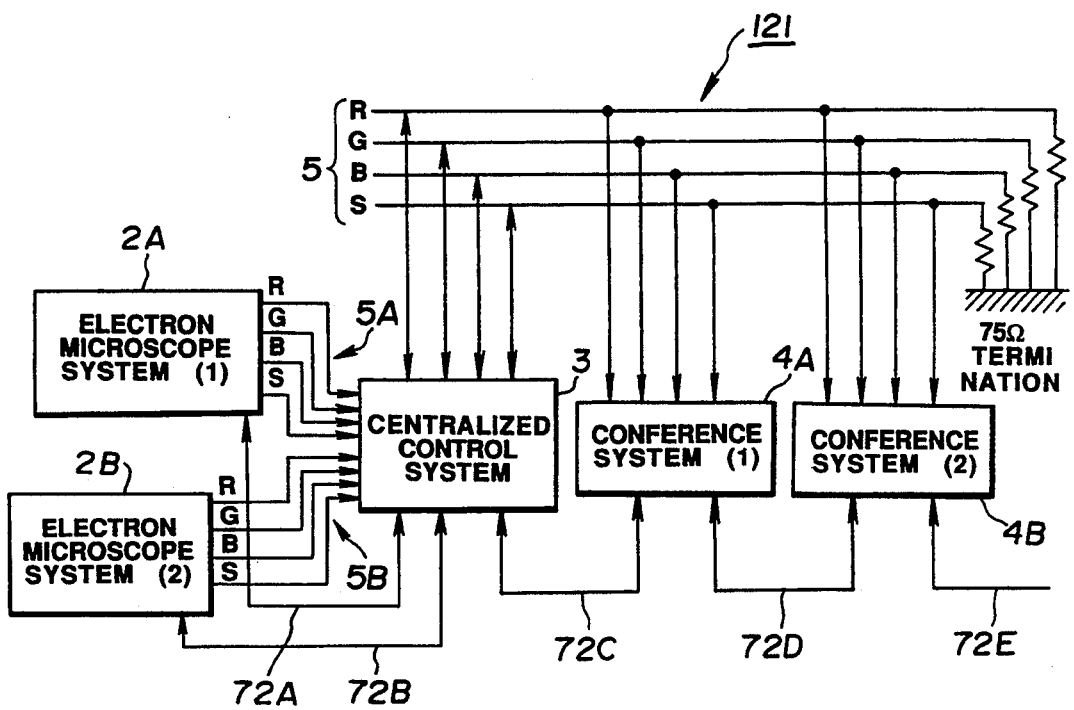
FIGS. 32 to 34 each show a tenth embodiment of the present invention.

FIG. 32 shows a network system 121 according to a tenth embodiment of the present invention.

In this embodiment, RS-232C digital transmission lines 72C and 72D, which are the same as the lines 72C and 72D between the centralized control system 3 and the conference systems (1) 4A and (2) 4B in the second embodiment shown in FIG. 6, are connected in file as shown in FIG. 32.

In other words, a centralized control system 3 is connected to a first RS-232C port of a conference system (1) 4A through an RS-232C digital transmission line 72C, and a second RS-232C port of the conference system (1) 4A is connected to a first RS-232C port of a conference system (2) 4B through an RS-232C digital transmission line 72D.

If the next conference system is disposed, a second RS-232C port of the conference system (2) 4B is connected to the next conference system through an RS-232C digital transmission line 72E.

Figure 33:
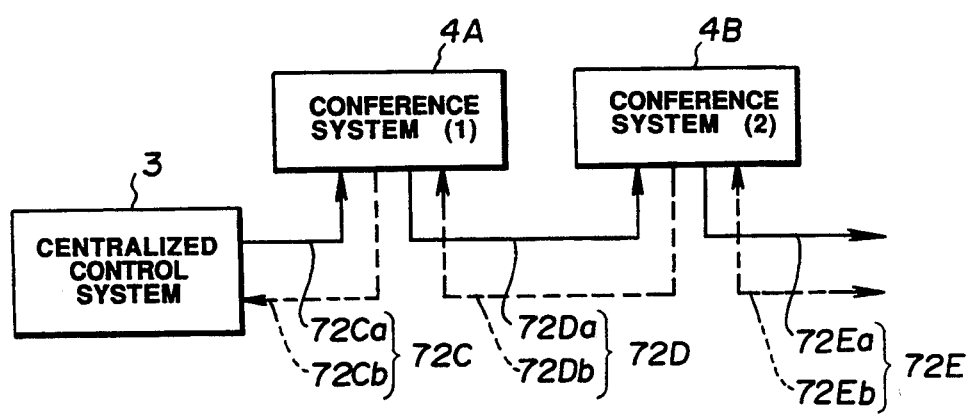

FIG. 33 is an enlarged view of the principal part of FIG. 32. A control signal and so on can be transmitted from the centralized control system 3 to the conference system (1) 4A through a transmission line 72Ca in the RS-232C digital transmission line 72C extending from the centralized control system 3. Furthermore, the control signal and so on which are transmitted to the conference system (1) 4A can be transmitted to the conference system (2) 4B through a transmission line 72Da in the RS-232C digital transmission line 72D which links the conference systems (1) 4A and (2) 4B.

A control signal and so on can be transmitted from the conference system (2) 4B to the next conference system through a transmission line 72Ea. Thus, the transmission of a control signal and so on from the centralized control system 3 to an arbitrary conference system 4I (I=A, B, . . . ) through the conference systems 4A, 4B, . . . is possible.

The conference system (2) 4B can transmit a reply signal and so on to the conference system (1) 4A through a receiving line 72Db. The conference system (1) 4A can send a reply signal and so on to the centralized control system 3 through a receiving line 72Cb, and transfer the reply signal and so on transmitted through the signal receiving line 72Db. If another conference system is mounted, the conference system (2) 4B transfers a reply signal and so on transmitted through a signal receiving line 72Eb to the conference system (1) 4A.

Figure 34A:
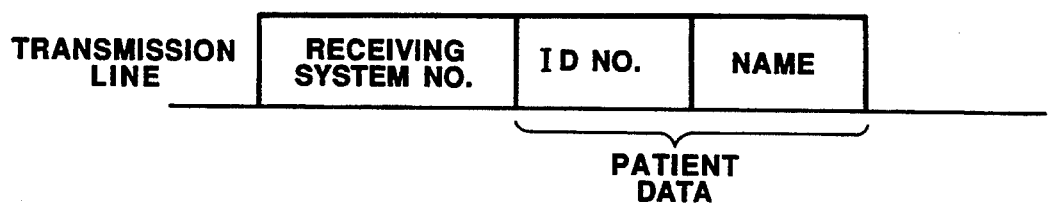

FIG. 34a shows an example of the contents transmitted by the signal transmission line 72Ca and so on.

In other words, the transmission side (for example, the centralized control system 3) transmits a receiving system No. for designating the number of a system to be selected, and then patient data including the ID No. and the name NAME of a patient.

Figure 34B:
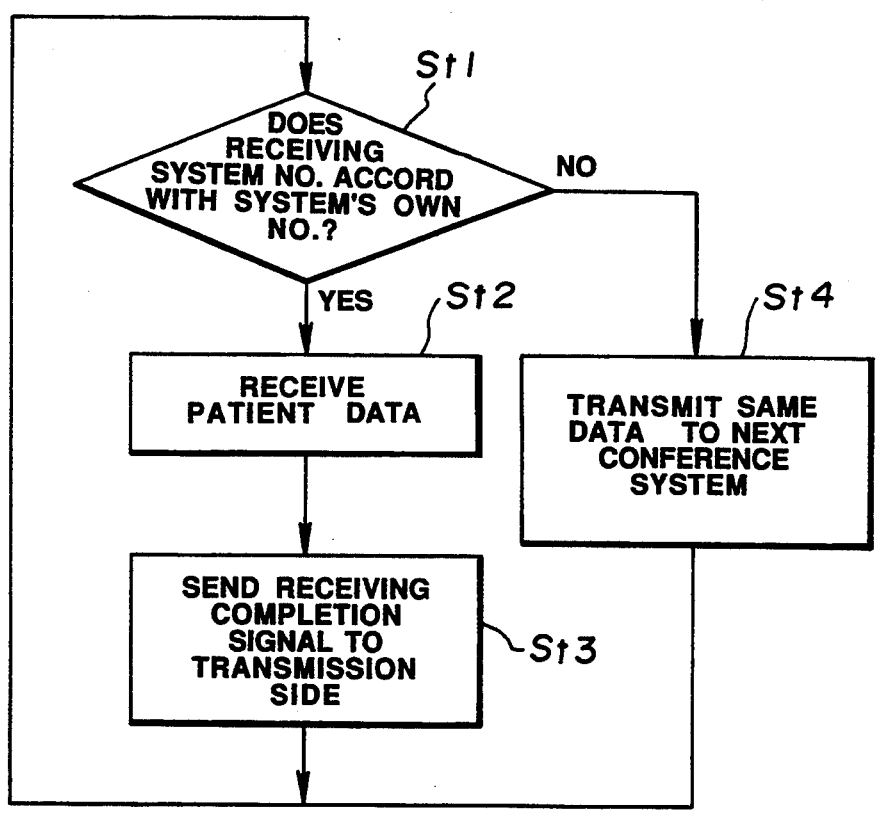

On the other hand, the conference systems conduct processes shown in FIG. 34b on the data transmitted by the transmission lines 72Ca, 72Da, . . .

In other words, a controller 64 executes Step St1 of checking whether the receiving system No. received from the transmission lines 72Ca, 72Da, . . . accords with its own system number. If both the numbers accord, Step St2 of receiving the patient data in the transmitted data is executed. Subsequently, Step St3 of sending back a reply signal indicating the completion of receiving through the receiving lines 72Cb, 72Db, . . . is executed.

On the other hand, if the answer is NO in the above Step St1, Step St4 of transmitting (transferring) the same data to the next conference system is carried out.

The above operations will now be specifically described with reference to, for example, a case in which patient data is sent from the centralized control system 3 to the conference system (2) 4B and the centralized control system 3 receives reply data from the conference system (2) 4B.

(1) The centralized control system 3 sends a receiving system No. of 2 as data shown in FIG. 34a to the conference system (1) 4A.

(2) The conference system (1) 4A detects the receiving system No. Since the receiving system No. is different from its own system No., the conference system (1) 4A transmits the same data to the next system, that is, the conference system (2) 4B.

(3) The conference system (2) 4B detects the receiving system No., and receives the patient data since it determines that the receiving system No. accords with its own system No. When the receiving operation is completed, the conference system (2) 4B returns a command indicating the completion to the conference system (1) 4A, and turns to an analog image receiving state.

(4) The conference system (1) 4A sends the command, as it stands, from the conference system (2) 4B in the above (3) to the centralized control system 3.

(5) On receiving the command, the centralized control system 3 sends an RGB image to the analog transmission line 5.

(6) The conference system (2) 4B monitors an SYNC signal, takes RGB information in an R, G and B frame memory 62 in synchronization with the SYNC signal, and displays the RGB information on a monitor 67 or records the RGB information on a magneto-optical disk.

According to this embodiment, the number of RS-232C digital transmission lines can be decreased. In other words, the lines 72C and 72D necessary between the centralized control system 3 and the conference systems (1) 4A and (2) 4B can be replaced with a single line.

Figure 35:
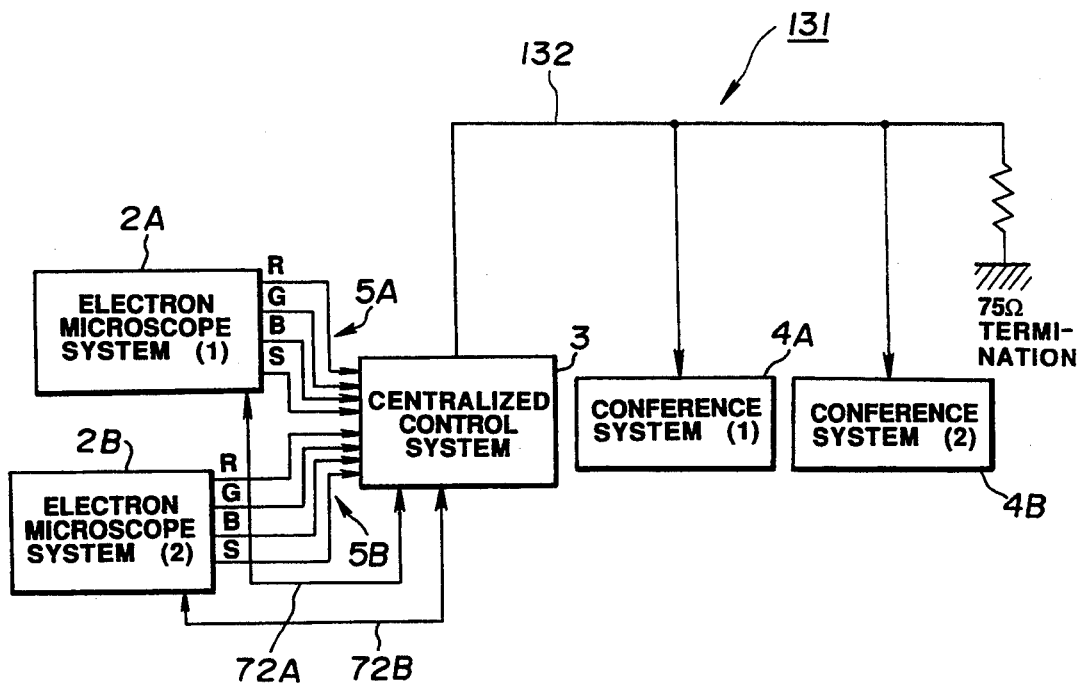
FIGS. 35 to 38 each show an eleventh embodiment of the present invention.

FIG. 35 shows a network system 131 according to an eleventh embodiment of the present invention.

The eleventh embodiment is an improvement of the second embodiment, and transmits both R, G and B image information and patient information through a single coaxial line 132.

In an ordinary endoscopic examination, electron microscope systems (1) 2A and (2) 2B and a centralized control system 3 are arranged in close relation and, on the other hand, a conference room is often located apart from the above systems, for example, in a building separate from a building where the systems are installed. In such a case, it is extremely advantageous that the number of cables to be laid is small.

Figure 36:
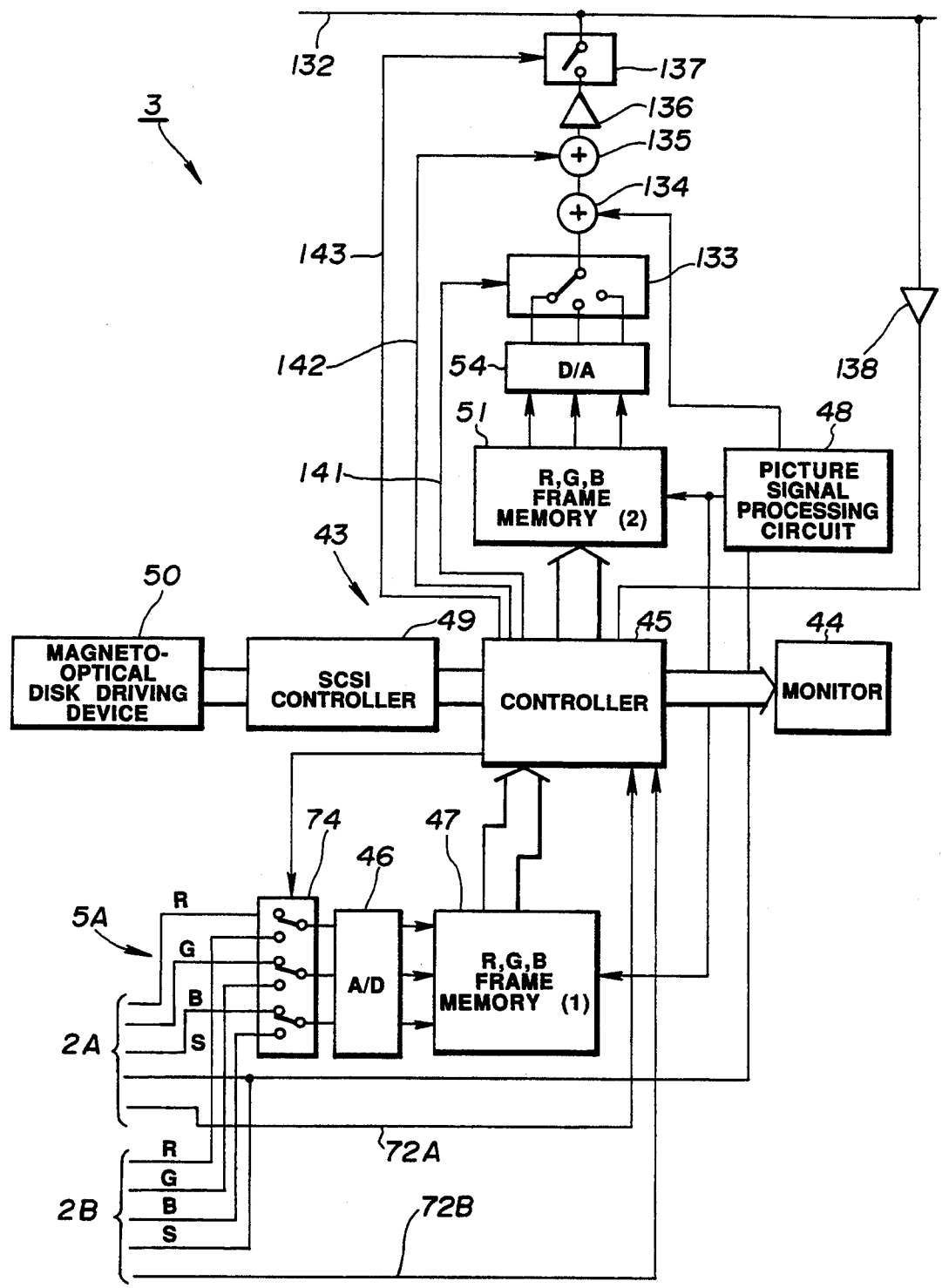

The construction of the centralized control system 3 in this embodiment is shown in FIG. 36.

In the centralized control system 3, an output terminal of a D/A converter 54, which is the same as the D/A converter 54 shown in FIG. 8, is connected to an input terminal of a first adder 134 through a select switch 133, and an output terminal of the adder 134 is connected to an input terminal of a second adder 135. The output of the adder 135 is applied to the coaxial line 132 as a transmission line through a buffer 136 and a switch 137.

Furthermore, a reply signal sent from the conference system through the coaxial line 132 is input to a controller 45 through a receiving buffer 138.

The select switch 133 is controlled by a signal from the controller 45 through an RGB switch signal line 141. An SYNC signal from a picture signal processing circuit 48 is added to the first adder 134. The second adder 135 adds patient data transmitted from the controller 45 through a patient data transmission line 142 to the output of the first adder 134. Furthermore, the switch 137 is controlled by a control signal from the controller 45 through a transmission line transmission control signal line 143.

Figure 37:
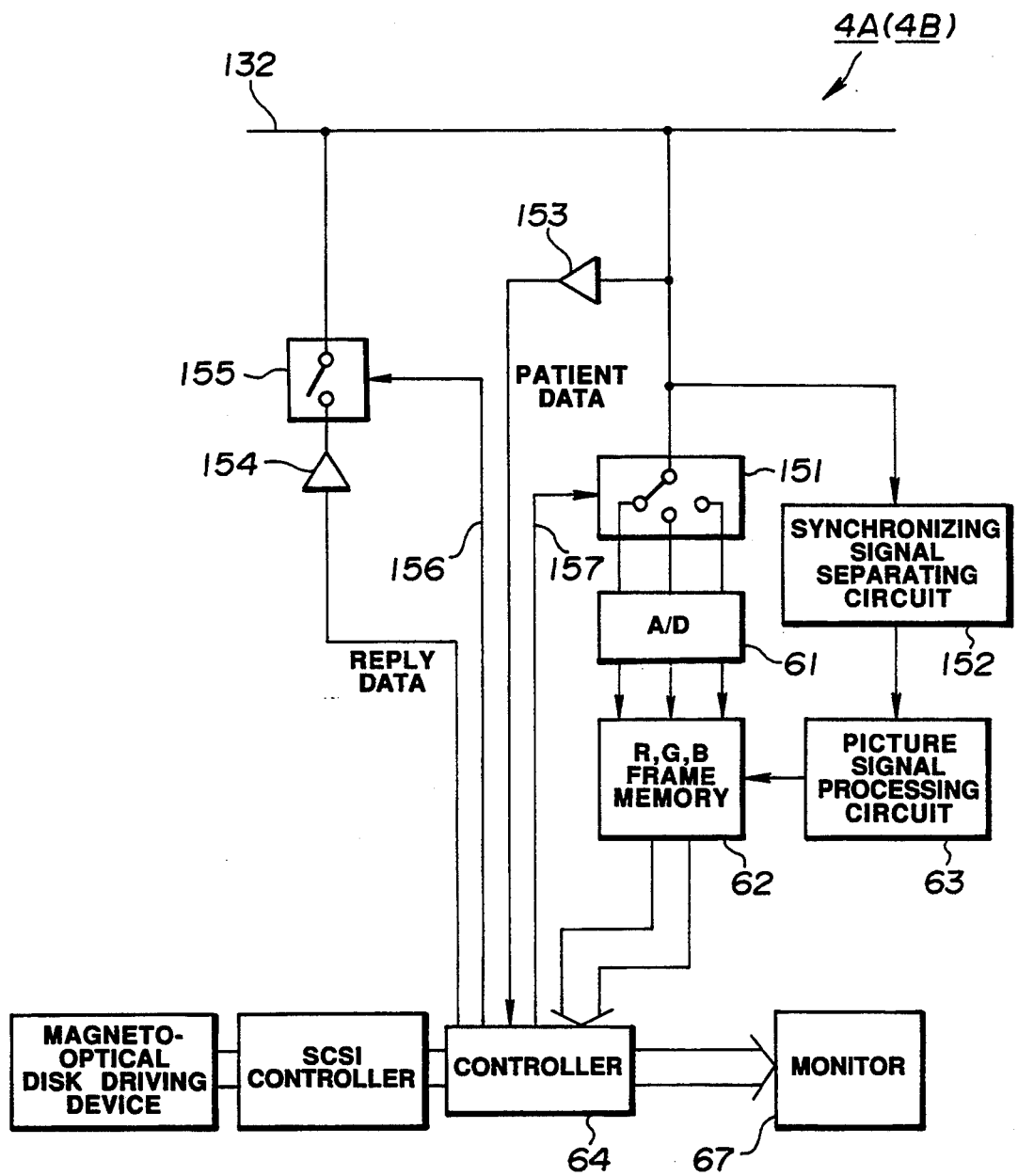

The conference system (1) 4A or (2) 4B has the construction shown in FIG. 37.

An input terminal of an A/D converter 61, which is the same as the A/D converter 61 shown in FIG. 9, is connected to the coaxial line 132 through a select switch 151. The coaxial line 132 is connected to a synchronizing signal separating circuit 152, which picks out and outputs an SYNC signal to a picture signal processing circuit 63. Furthermore, the coaxial line 132 is connected to a controller 64 through a buffer 153 so as to output transmitted patient data to the controller 64.

Figure 38:
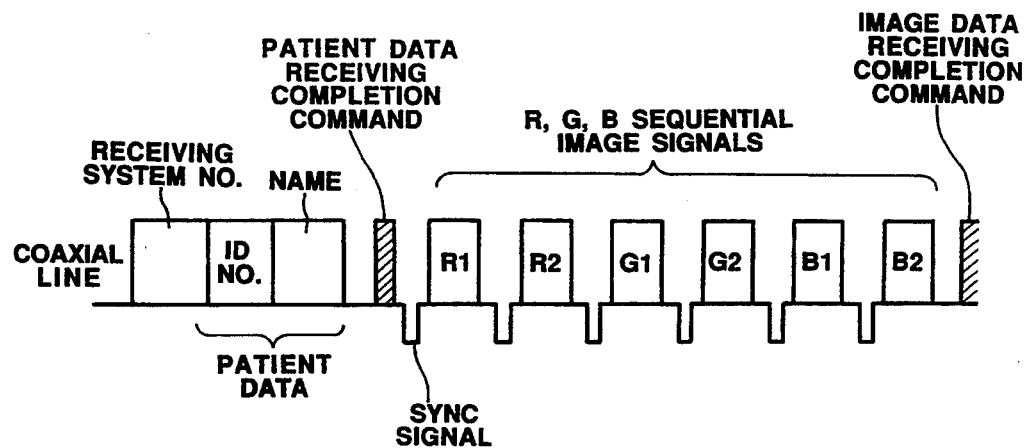

The controller 64 can send a reply command indicating the completion of receiving through a buffer 154 and a switch 155 after receiving patient data and image data as shown in FIG. 38. The opening and closing of the switch 155 is controlled by a control signal from the controller 64 through a transmission control line 156. The select switch 151 is controlled by a select switch through an RGB switch signal line 157. The same components as those of the system (1) 4A or (2) 4B shown in FIG. 9 are denoted by like numerals, and the description of the components is omitted. FIG. 38 shows an example of the transmission form of image and patient data transmitted through the coaxial line 132 according to the eleventh embodiment.

The centralized control system 3 transmits the receiving system No. and patient data through the coaxial line 132. When the conference system having the receiving system No. completes a receiving operation, it returns a patient data receiving completion command through the coaxial line 132. When receiving the completion command, the centralized control system 3 transmits sequential R, G and B image signals in synchronization with an SYNC signal. On receiving the image signals, the conference system sends an image receiving completion command through the coaxial line 132. According to the eleventh embodiment, since only the single coaxial line 132 is necessary instead of the R, G and B lines between the centralized control system 3 and the conference systems (1) 4A and (2) 4B and the S line, the number of cables to be laid can be decreased.

Although the R, G and B signals are transmitted in the above embodiments, the present invention is applicable to Y/C separation and transmission by a composite video signal.

The number of component systems (for example, the number of conference systems) in the present invention is not limited to the above-mentioned ones.

An embodiment obtained by partially combining the above-mentioned embodiments is included in the present invention.

What is claimed is:

1. A medical network system, comprising:
   an image sending device for sending medical image information;
   an image receiving device for receiving said medical image information;
   a common analog transmission line directly connecting said image sending device and said image receiving device for transmitting in analog form a medical image signal corresponding to a medical image as said medical image information, and a synchronizing signal in synchronization with said medical image signal between said image sending device and said image receiving device; and
   control means connected to said common analog transmission line for controlling the transmission of said medical image information through said common analog transmission line by a digital signal,
   wherein said control means includes an image sending and receiving means capable of sending and receiving said medical image information, wherein said control means further includes an image information recording means for recording said medical information, and
   wherein said control means controls the transmission of said medical image information between said image sending device, said image receiving device and said image information recording means.

2. A medical network system according to claim 1, wherein said analog transmission line has a first line for transmitting said medical image signal and a second line for transmitting said synchronizing signal.

3. A medical network system according to claim 1, wherein said analog transmission line transmits said medical image signal and said synchronizing signal through a common line.

4. A medical network system according to claim 1, wherein said analog transmission line transmits a color medical image signal corresponding to a color medical image as said medical image information.

5. A medical network system according to claim 4, wherein said analog transmission line separates said color medical image signal into a plurality of color signals and transmits said separated color signals.

6. A medical network system according to claim 5, wherein said analog transmission line transmits said plurality of color signals through a plurality of transmission lines.

7. A medical network system according to claim 5, wherein said analog transmission line transmits said separated plurality of color signals while superimposing said color signals in time sharing.

8. A medical network system, comprising:
an image sending device for sending medical image information;
an image receiving device for receiving said medical image information;
at least one image sending/receiving device for sending or receiving said medical image information; and
a centralized control device connected to said image sending device, said image receiving device and said image sending/receiving device through a carrier analog transmission line for transmitting said medical image information in analog form, said centralized control device centrally controlling the transmission of said medical image information through said analog transmission line by using a digital signal,
wherein said centralized device, said image sending device, said image receiving device and said image sending/receiving device are directly connected simultaneously through said common analog transmission line,
wherein said centralized control device includes an image sending and receiving device capable of sending and receiving said medical image information,
wherein said centralized control device further includes image recording and reproducing means for recording and reproducing said medical image information, and
wherein said centralized control device controls the transmission of said medical image information between said image sending device, said image receiving device, said at least one image sending/receiving device, and said image recording and reproducing means.

9. A medical network system according to claim 8, wherein said medical image information transmitted through said analog transmission line is endoscopic image information.

10. A medical network system according to claim 8, wherein said medical image information transmitted through said analog transmission line is color endoscopic image information.

* * * * *